United States Patent [19]

Emonds-Alt et al.

[11] Patent Number: 5,625,060
[45] Date of Patent: Apr. 29, 1997

[54] POLYCYCLIC AMINE COMPOUNDS AND THEIR ENANTIOMERS, THEIR METHOD OF PREPARATION AND PHARMACEUTICAL COMPOSITIONS ON WHICH THEY ARE PRESENT

[75] Inventors: Xavier Emonds-Alt, Combaillaux; Patrick Gueule, Teyrand; Vincenzo Proietto, Saint Georges D'Orques; Pierre Goulaouic, deceased, late of Montpellier; Marie Bousquet, legal representative, Bourg la Reine; Catherine M. L. Goulaouic, legal representative, Gif sur Yvette, all of France

[73] Assignee: Elf Sanofi, Paris, France

[21] Appl. No.: 463,270

[22] Filed: Jun. 5, 1995

Related U.S. Application Data

[62] Division of Ser. No. 261,269, Jun. 15, 1994, which is a division of Ser. No. 878,710, May 4, 1992, Pat. No. 5,340,822.

[30] Foreign Application Priority Data

May 3, 1991 [FR] France .................. 91 05487

[51] Int. Cl.$^6$ ............... C07D 401/02; C07D 401/14; A61K 31/445; A61K 31/55
[52] U.S. Cl. ............. 540/524; 540/597; 540/598; 546/186; 546/188; 546/189; 546/208; 546/190; 546/191; 544/121; 544/122; 544/129; 544/333; 544/357; 544/359; 544/360; 544/365; 544/372
[58] Field of Search ............... 546/186, 188, 546/189, 208; 540/524, 597, 598

[56] References Cited

U.S. PATENT DOCUMENTS

| | | | |
|---|---|---|---|
| 3,562,281 | 2/1971 | Werner et al. | 546/189 |
| 3,718,743 | 2/1973 | Shen et al. | 424/267 |
| 4,094,987 | 6/1978 | Hasspacher et al. | 424/274 |
| 4,948,799 | 8/1990 | Antoku et al. | 514/278 |

FOREIGN PATENT DOCUMENTS

| | | |
|---|---|---|
| 0347802 | 12/1989 | European Pat. Off. . |
| 0412542 | 2/1991 | European Pat. Off. . |
| 2345192 | 3/1974 | Germany . |
| 2056439 | 3/1981 | United Kingdom . |

OTHER PUBLICATIONS

H. Bochow et al., Chem Ber. 198, 3475–3482 (1975) "4-Phenyl-2-chinuclidinol".

Bellstein, Ref. No. 5-23-03-00125, Reg. No. 827129 (1968).

*Primary Examiner*—Mukund J. Shah
*Assistant Examiner*—King Lit Wong
*Attorney, Agent, or Firm*—Foley & Lardner

[57] ABSTRACT

The invention relates to polycyclic amine compounds of formula (I)

$$Y-(b)-N-(CH_2)_m-C(Ar')(CH_2)_p(CH_2)_n-Q-N-T-(CH_2)_q-Z \quad (I)$$

and their enantiomers, useful as neurokinin receptor antagonists.

5 Claims, No Drawings

POLYCYCLIC AMINE COMPOUNDS AND THEIR ENANTIOMERS, THEIR METHOD OF PREPARATION AND PHARMACEUTICAL COMPOSITIONS ON WHICH THEY ARE PRESENT

This application is a division, of application Ser. No. 08/261,269, filed Jun. 15, 1994, which is a division of application Ser. No. 07/878,710, filed May 4, 1992, now U.S. Pat. No. 5,340,822.

The present invention relates to novel aromatic derivatives substituted by an amino group and by amine or amide groups, and their enantiomers.

The present invention further relates to the method of obtaining the compounds, which can be enantioselective, and to the use of the compounds according to the invention in compositions for use in therapeutics and more particularly in pathological phenomena involving the neurokinin system, such as: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, U.S. and Pernow ed., 287–293, Raven Press, New York), gastrointestinal disorders (D. Regoli et al., Trends Pharmacol. Sci., 1985, 6, 481–484) and respiratory disorders (J. Mizrahi et al., Pharmacology, 1982, 25, 39–50).

Ligands endogenous to neurokinin receptors have been described, such as substance P (SP), neurokinin A (NKA) (S. J. Bailey et al., 1983, Substance P, P. Skrabanck ed., 16–17 Boole Press, Dublin) and neurokinin B (NKB) (S. P. Watson, Life Sciences, 1983, 25, 797–808).

Neurokinin receptors have been recognized on numerous preparations and are currently classed in three types: $NK_1$, $NK_2$ and $NK_3$. Whereas the majority of preparations studied hitherto have several types of receptors, such as guinea-pig ileum ($NK_1$, $NK_2$ and $NK_3$), some of them are thought to possess only one type, such as dog carotid artery ($NK_1$), rabbit pulmonary artery devoid of endothelium ($NK_2$) and rat portal vein ($NK_3$) (D. Regoli et al., Trends Pharmacol. Sci., 1988, 9, 290–295, and Pharmacology, 1989, 38, 1–15).

The recent synthesis of selective agonists has made it possible to characterize the various receptors more precisely. Thus $[Sar^9,Met-(O_2)^{11}]SP$, $[Nle^{10}]-NKA_{4-10}$ and $[MePhe^7]$ NKB are thought to have a selectivity for the $NK_1$, $NK_2$ and $NK_3$ receptors respectively (cf. D. Regoli, 1988 and 1989, op. cit.).

It has now been found that certain aromatic amine compounds possess valuable pharmacological properties as neurokinin receptor antagonists and are especially useful for the treatment of any substance P-dependent and neurokinin-dependent pathological condition.

Thus, according to one of its features, the present invention relates to aromatic amine derivatives of the formula

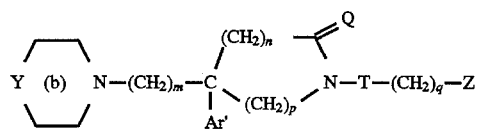

in which:

Y is either a group Cy-N or Cy-CH$_2$-N, in which:

Cy is a phenyl which is unsubstituted or monosubstituted or polysubstituted by a substituent selected from: a halogen atom, a hydroxyl, a $C_1$–$C_4$ alkoxy, a $C_1$–$C_4$ alkyl and a trifluoromethyl, said substituents being identical or different; a $C_3$–$C_7$ cycloalkyl group; a pyrimidyl group or a pyridyl group;

or a group

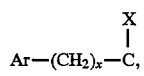

in which:

Ar is a phenyl which is unsubstituted or monosubstotited or polysubstituted by a substituent selected from: hydrogen, a halogen atom, a hydroxyl, a $C_1$–$C_4$ alkoxy, a trifluoromethyl and a $C_1$–$C_4$ alkyl, said substituents being identical or different; a pyridyl group or a thienyl group;

x is zero or one; and

X is a hydrogen; a hydroxyl; a $C_1$–$C_4$ alkoxy; a $C_1$–$C_4$ acyloxy; a carboxyl; a $C_1$–$C_4$ carbalkoxy; a cyano; a group —N(X$_1$)$_2$, in which the groups X$_1$ independently are hydrogen, a $C_1$–$C_4$ alkyl, a $C_1$–$C_4$ hydroxyalkyl or a $C_1$–$C_4$ acyl, or else —(X$_1$)$_2$ forms, with the nitrogen atom to which it is bonded, a heterocycle selected from pyrrolidine, piperidine or morpholine; or a group —S—X$_2$, in which X$_2$ is hydrogen or a $C_1$–$C_4$ alkyl group;

or else X forms a double bond with the carbon atom to which it is bonded and with the adjacent carbon atom in the heterocycle;

m is 2 or 3;

Ar' is a phenyl which is unsubstituted or monosubstituted or polysubstituted by a substituent selected from: a halogen atom, preferably a chlorine or fluorine atom, a trifluoromethyl, a $C_1$–$C_4$ alkoxy and a $C_1$–$C_4$ alkyl, said substituents being identical or different; a thienyl; a benzothienyl; a naphthyl or an indolyl;

n is 0, 1, 2 or 3;

p is 1 or 2, and when p is equal to 2, n is then equal to 1 and Q is two hydrogen atoms;

Q is oxygen or two hydrogen atoms;

T is a group selected from

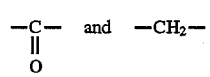

q is 0, 1, 2 or 3; and

Z is a phenyl which is unsubstituted or monosubstituted or polysubstituted by a halogen atom, more particularly a chlorine or fluorine atom, a trifluoro-methyl, a $C_1$–$C_4$ alkyl, a hydroxyl or a $C_1$–$C_4$ alkoxy; a naphthyl which is unsubstituted or monosubstituted or polysubstituted by a halogen, a trifluoromethyl, a $C_1$–$C_4$ alkyl or a hydroxyl; a pyridyl; a thienyl; an indolyl; a quinolyl; a benzothienyl. or an imidazolyl; or else when T is —C═O, —(CH$_2$)$_q$-Z can also be a benzyl group substituted on the —CH— by a hydroxyl, a $C_1$–$C_4$ alkoxy or a $C_1$–$C_4$ alkyl and unsubstituted or substituted on the aromatic ring by a halogen, more particularly a chlorine or fluorine atom, a tri-fluoromethyl, a $C_1$–$C_4$ alkyl, a hydroxyl or a $C_1$–$C_4$ alkoxy; or a substituted or unsubstituted mono-, di- or tri-cyclic aromatic or heteroaromatic group;

or, if appropriate, one of their salts with mineral or organic acids, or, when

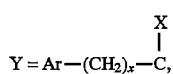

a quaternary ammonium salt or an N-oxide derivative formed with nitrogen (b) of the piperidine.

In the present description the alkyl groups or the alkoxy groups are linear or branched.

The salts of the compounds of formula (I) according to the present invention include those with mineral or organic acids which permit a suitable separation or crystallization of the compounds of formula (I), such as picric acid, oxalic acid or an optically active acid, for example a mandelic or camphosulfonic acid, as well as those which form pharmaceutically acceptable salts such as the hydrochloride, hydrobromide, sulfate, hydrogensulfate, dihydrogenphosphate, methanesulfonate, methylsulfate, maleate, fumarate, naphthalene-2-sulfonate, glycolate, gluconate, citrate and isethionate.

When

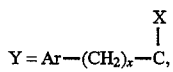

the compounds of formula (I) can be in the form of a quaternary ammonium salt formed with nitrogen (b) of the piperidine or an N-oxide derivative formed with nitrogen (b), in which case the group

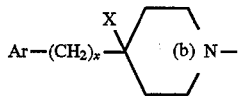

is represented by the group

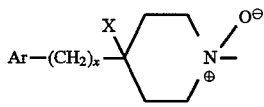

or the group

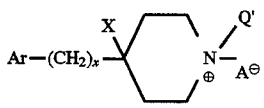

in which:

Q' is a $C_1$–$C_6$ alkyl group or a benzyl group, and

A$\ominus$ is an anion selected from chloride, bromide, iodide, acetate, methanesulfonate or paratoluenesulfonate.

In particular, Z in formula (I) is a mono-, di- or tri-cyclic aromatic or heteroaromatic group which can carry one or more substituents and in which a carbon atom of the aromatic carbocycle or of the aromatic heterocycle is directly bonded to the group T.

More particularly, the radical Z can be a phenyl group or a benzyl group which can be unsubstituted or may contain one or more substituents.

When Z is a phenyl group, this can preferably be monosubstituted or disubstituted, especially in the 2,4 positions, but also for example in the 2,3, 4,5, 3,4 or 3,5 positions; it can also be trisubstituted, especially in the 2,4,6 positions, but also for example in the 2,3,4, 2,3,5, 2,4,5 or 3,4,5 positions, tetrasubstituted, for example in the 2,3,4,5 positions, or pentasubstituted. The substituents of the phenyl group can be: F; Cl; Br; I; CN; OH; $NH_2$; $NH$—$CONH_2$; $NO_2$; $CONH_2$; $CF_3$; $C_1$–$C_{10}$ alkyl, preferably $C_1$–$C_4$ alkyl, methyl or ethyl being preferred, as well as, for example, n-propyl, isopropyl, n-butyl, isobutyl, sec-butyl, tert-butyl, pentyl or n-pentyl, hexyl or n-hexyl, heptyl or n-heptyl, octyl or n-octyl, nonyl or n-nonyl or decyl or n-decyl; alkenyl containing 2 to 10 carbon atoms, preferably 2–4 carbon atoms, for example vinyl, allyl, prop-1-enyl, isopropenyl, butenyl or but-1-en-1-, -2-, -3- or -4-yl, but-2-en-1-yl, but-2-en-2-yl, pentenyl, hexenyl or decenyl; alkynyl containing 2 to 10 carbon atoms, preferably 2–4 carbon atoms, for example ethynyl, prop-1-yn-1-yl, propargyl, butynyl or but-2-yn-1-yl, pentynyl or decynyl; cycloalkyl containing 3 to 8 carbon atoms, preferably 5 or 6 carbon atoms, cyclopentyl or cyclohexyl being preferred, as well as, for example, cyclopropyl, cyclobutyl, 1-, 2- or 3-methylcyclopentyl, 1-, 2-, 3- or 4-methylcyclohexyl, cycloheptyl or cyclooctyl; bicycloalkyl containing 4 to 11 carbon atoms, preferably 7 carbon atoms, exo- or endo-2-norbornyl being preferred, as well as, for example, 2-isobornyl or 5-camphyl; hydroxyalkyl containing 1 to 5 carbon atoms, preferably 1–2 carbon atoms, hydroxymethyl and 1- or 2-hydroxyethyl being preferred, as well as, for example, 1-hydroxyprop-1-yl, 2-hydroxyprop-1-yl, 3-hydroxyprop-1-yl, 1-hydroxyprop-2-yl, 1-hydroxybut-1-yl or 1-hydroxypent-1-yl; alkoxy containing 1 to 10 carbon atoms, preferably 1–4 carbon atoms, methoxy, ethoxy or isopropoxy being preferred, as well as, for example, n-propoxy, n-butoxy, isobutoxy, sec-butoxy, tert-butoxy, pentoxy, hexyloxy, heptyloxy, octyloxy, nonyloxy or decyloxy; alkoxyalkyl containing 2 to 10 carbon atoms, preferably from 2 to 6 carbon atoms, for example alkoxymethyl or alkoxyethyl, such as methoxymethyl or 1- or 2-methoxyethyl, 1- or 2-n-butoxyethyl or 1- or 2-n-octyloxyethyl; alkoxyalkoxyalkyl containing up to 10 carbon atoms, preferably from 4 to 7 carbon atoms, for example alkoxyalkoxymethyl such as 2-methoxyethoxymethyl, 2-ethoxyethoxymethyl or 2-isopropoxyethoxymethyl, or alkoxyalkoxyethyl such as 2-(2-methoxyethoxy)ethyl or 2-(2-ethoxyethoxy)ethyl; alkoxyalkoxy containing from 2 to 10 carbon atoms, preferably from 3 to 6 carbon atoms, for example 2-methoxyethoxy, 2-ethoxyethoxy or 2-n-butoxyethoxy; alkenyloxy containing 2 to 10 carbon atoms, preferably 2 to 4 carbon atoms, allyloxy being preferred, as well as, for example, vinyloxy, propenyloxy, isopropenyloxy, butenyloxy such as but-1-en-1-, -2-, -3- or -4-yloxy, but-2-en-1-yloxy or but-2-en-2-yloxy, pentenyloxy, hexenyloxy or decenyloxy; alkenyloxyalkyl containing from 3 to 10 carbon atoms, preferably 3–6 carbon atoms, for example allyloxymethyl; alkynyloxy containing from 2 to 10 carbon atoms, preferably 2 to 4 carbon atoms, propargyloxy being preferred, as well as, for example, ethynyloxy, prop-1-yn-1-yloxy, butynyloxy or but-2-yn-1-yloxy, pentynyloxy or decynyloxy; alkynyloxyalkyl containing from 3 to 10 carbon atoms, preferably 3 to 6 carbon atoms, for example ethynyloxymethyl, propargyloxymethyl or 2-(but-2-yn-1-yloxy)ethyl; cycloalkoxy containing 3 to 8 carbon atoms, preferably 5 or 6 carbon atoms, cyclopentoxy or cyclohexyloxy being preferred, as well as, for example, cyclopropoxy, cyclobutoxy, 1-, 2- or 3-methylcyclopentoxy, 1-, 2-, 3- or 4-methylcyclohexyloxy, cycloheptyloxy or cyclooctyloxy; alkylthio containing from 1 to 10 carbon atoms, preferably 1 to 4 carbon atoms, methylthio or ethylthio being preferred, as well as, for example, n-propylthio, isopropylthio, n-butylthio, isobutylthio, sec-butylthio, tert-butylthio, pentylthio, hexylthio, octylthio, nonylthio or decylthio; alkylthioalkyl containing from 2 to 10 carbon atoms, preferably 2 to 6 carbon atoms, for example methylthiomethyl, 2-methylthioethyl or 2-n-butylthioethyl; acylamino, namely alkanoylamino containing from 1 to 7 carbon atoms, preferably 1 to 4 carbon atoms, formylamino and acetylamino being preferred, as well as propionylamino, butyrylamino, isobutyrylamino, valerylamino, caproylamino or heptanoylamino, or aroylamino or benzylamino; acylaminoalkyl, preferably alkanoylaminoalkyl containing from 2 to 8 carbon atoms, preferably 3 to 6 carbon atoms, such as formylaminoethyl, acetylaminoethyl, propionylaminoethyl, n-butyrylaminoethyl, formylaminopropyl, acetylaminopropyl, propionylaminopropyl, formylaminobutyl or acetylaminobutyl, as well as propionylaminobutyl or butyrylaminobutyl; acyloxy containing from 1 to 6 carbon atoms, preferably 2 to 4 carbon atoms, acetoxy, propionyloxy or butyryloxy being preferred, as well as, for example, formyloxy, valeryloxy or caproyloxy; alkoxycarbonyl containing from 2 to 5 carbon atoms, preferably 2 or 3 carbon atoms, methoxycarbonyl and ethoxycarbonyl being preferred, as well as, for example, n-propoxycarbonyl, isopropoxycarbonyl, n-butoxycarbonyl, isobutoxycarbonyl, sec-butoxycarbonyl or tert-butoxycarbonyl; cycloalkoxycarbonyl containing from 4 to 8 carbon atoms, preferably 6 or 7 carbon atoms, cyclopentoxycarbonyl and cyclohexyloxycarbonyl being preferred, as well as cyclopropoxycarbonyl, cyclobutoxycarbonyl or cycloheptyloxycarbonyl; alkylaminocarbonylamino containing from 2 to 4 carbon atoms, such as methylaminocarbonylamino, ethylaminocarbonylamino or propylaminocarbonylamino; dialkylaminocarbonylamino containing from 3 to 7 carbon atoms, preferably 3 to 5 carbon atoms, dimethylaminocarbonylamino being preferred, as well as di-n-propylaminocarbonylamino or diisopropylaminocarbonylamino; (pyrrolidin-1-yl)carbonylamino; cycloalkylaminocarbonylamino containing from 4 to 8 carbon atoms, preferably 6 or 7 carbon atoms, cyclopentylaminocarbonylamino and cyclohexylaminocarbonylamino being preferred, as well as cyclopropylaminocarbonylamino, cyclobutylaminocarbonylamino or cycloheptylaminocarbonylamino; alkylaminocarbonylaminoalkyl containing from 3 to 9 carbon atoms, preferably 4 to 7 carbon atoms, methylaminocarbonylaminoethyl, ethylaminocarbenylaminoethyl, ethylaminocarbonylaminopropyl and ethylaminocarbonylaminobutyl being preferred, as well as, for example, methylaminocarbonylaminomethyl, n-propylaminocarbonylaminobutyl and n-butylaminocarbonylaminobutyl; dialkylaminocarbonylaminoalkyl containing from 4 to 11 carbon atoms, for example dimethylaminocarbonylaminomethyl, diethylaminocarbonylaminoethyl, diethylaminocarbonylaminopropyl and diethylaminocarbonylaminobutyl; (pyrrolidin-1-yl)carbonylaminoethyl; (piperidin-1-yl)carbonylaminoethyl; cycloalkylaminocarbonylaminoalkyl containing from 5 to 12 carbon atoms, preferably 8 to 11 carbon atoms, cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl being preferred, as well as, for example, cyclopropylaminocarbonylaminomethyl or cycloheptylaminocarbonylaminoethyl; alkoxycarbonylaminoalkyl containing from 3 to 12 carbon atoms, preferably 4 to 9 carbon atoms, methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec-butoxycarbonylaminoethyl, tert-butoxycarbonylaminoethyl, ethoxycarbonylaminopropyl, n-butoxycarbonylaminopropyl, ethoxycarbonylaminobutyl and n-butoxycarbonylaminobutyl being preferred, as well as, for example, n-propoxycarbonylaminopropyl, n-propoxycarbonylaminobutyl or isopropoxycarbonylaminobutyl; cycloalkoxycarbonylaminoalkyl containing from 5 to 12 carbon atoms, preferably 8 to 11 carbon atoms, cyclopentoxycarbonylaminoethyl, cyclopentoxycarbonylaminopropyl, cyclopentoxycarbonylaminobutyl, cyclohexyloxycarbonylaminoethyl, cyclohexyloxycarbonylaminopropyl and cyclohexyloxycarbonylaminobutyl being preferred, as well as, for example, cyclopropoxycarbonylaminomethyl or cycloheptyloxycarbonylaminoethyl; carbamoylalkyl containing from 2 to 5 carbon atoms, preferably 2 carbon atoms, carbamoylmethyl being preferred, as well as carbamoylethyl, carbamoylpropyl or carbemoylbutyl; alkylaminocarbonylalkyl containing from 3 to 9 carbon atoms, preferably 3 to 6 carbon atoms, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, sec-butylaminocarbonylmethyl and tert-butylaminocarbonylmethyl being preferred, as well as, for example, ethylaminocarbonylethyl, ethylaminocarbonylpropyl, ethylaminocarbonylbutyl, n-propylaminocarbonylbutyl or n-butylaminocarbonylbutyl; dialkylaminocarbonylalkyl containing from 4 to 11 carbon atoms, preferably 4 to 8 carbon atoms, dimethylaminocarbonylmethyl, diethylaminocarbonylmethyl and di-n-propylaminocarbonylmethyl being preferred, as well as, for example, diethylaminocarbonylethyl, diethylaminocarbonylpropyl or diethylaminocarbonylbutyl; (pyrrolidin-1-yl)carbonylmethyl; (piperidin-1-yl)carbonylmethyl; (piperidin-1-yl) carbonylethyl; cycloalkylaminocarbonylalkyl containing from 5 to 12 carbon atoms, preferably 7 or 8 carbon atoms, cyclopentylaminocarbonylmethyl and cyclohexylaminocarbonylmethyl being preferred, as well as, for example, cyclopropylaminocarbonylmethyl, cyclobutylaminocarbonylmethyl, cycloheptylaminocarbonylmethyl, cyclohexylaminocarbonylethyl, cyclohexylaminocarbonylpropyl or cyclohexylaminocarbonylbutyl; alkylaminocarbonylalkoxy containing from 3 to 10 carbon atoms, preferably 3 to 5 carbon atoms, methylaminocarbonylmethoxy being preferred, as well as, for example, methylaminocarbonylethoxy or methylaminocarbonylpropoxy; dialkylaminocarbonylalkoxy containing from 4 to 10 carbon atoms, preferably 4 to 7 carbon atoms, such as dimethylaminocarbonylmethoxy or diethylaminocarbonylethoxy; (piperidin-1-yl)carbonylmethoxy; and cycloalkylaminocarbonylalkoxy containing from 5 to 11 carbon atoms, preferably 7 or 8 carbon atoms, such as cyclopentylaminocarbonylmethoxy or cyclohexylaminocarbonylmethoxy.

The group Z is advantageously a phenyl group; a benzyl group; a benzoyl group; a phenylthioalkyl group in which the alkyl is $C_1$–$C_3$; or a naphthyl group.

The phenyl group Z is preferably monosubstituted or disubstituted by a halogen or an alkoxy, the isopropoxy group being preferred.

The radical Z can also be a bicyclic aromatic group such as naphth-1- or -2-yl or inden-1-, -2-, -3-, -4-, -5-, -6- or -7-yl, in which one or more bonds can be hydrogenated, it being possible for said groups to be unsubstituted or to contain one or more substituents such as: a halogen, and more particularly a fluorine atom, and alkyl, phenyl, cyano, hydroxyalkyl, hydroxy, oxo, alkylcarbonylamino, alkoxycarbonyl and thioalkyl groups, in which the alkyls are $C_1$–$C_4$.

The radical Z can also be a pyridyl, thiadiazolyl, indolyl, indazolyl, imidazolyl, benzimidazolyl, quinolyl, benzotriazolyl, benzofuranyl, benzothienyl, benzothiazolyl, benzisothiazolyl, isoquinolyl, benzoxazolyl, benzoxazinyl, benzodioxynyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl or chromanyl group, in which one or more double bonds can be hydrogenated, it being possible for said groups to be unsubstituted or to contain one or more substituents such as: alkyl, phenyl, cyano, hydroxyalkyl, hydroxyl, alkylcarbonylamino, alkoxycarbonyl and thioalkyl groups, in which the alkyls are $C_1$–$C_4$.

According to another feature, the present invention relates to a method of preparing the compounds of formula (I) and their salts, which comprises:

a) treating a compound of the formula

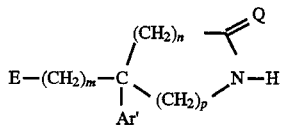

(II)

in which m, Ar', n, p and Q are as defined above and E is a hydroxyl or, if appropriate, an O-protected group such as, for example, tetrahydropyran-2-yloxy, or a group

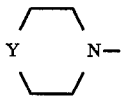

in which Y is as defined above, it being understood that: when Y is the group

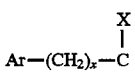

in which X is a hydroxyl, this hydroxyl can be protected, the compounds of formula (II) being novel compounds forming part of the invention, either with a functional derivative of an acid of the formula

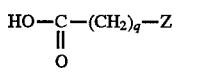

(III)

in which q and Z are as defined above, when a compound of formula (I) in which T is —CO— is to be prepared, or with a halogenated derivative of the formula

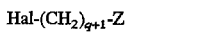

(IV)

in which q and Z are as defined above and Hal is a halogen, and preferably a bromine or chlorine atom, when a compound of formula (I) in which T is —$CH_2$— is to be prepared, to give the compound of the formula

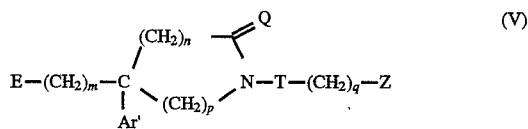

(V)

these compounds being novel compounds forming part of the invention, b) then, when E is a tetrahydropyranyloxy group, removing the tetrahydropyranyloxy group by reaction with an acid, c) treating the resulting alcohol of the formula

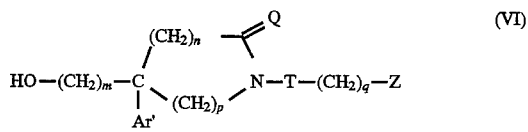

(VI)

these compounds being novel compounds forming part of the invention, with methanesulfonyl chloride, d) reacting the resulting mesylate of the formula

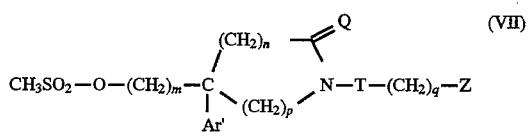

(VII)

these compounds being novel compounds forming part of the invention, with a secondary amine of the formula

(VIII)

in which Y is as defined above, and e) after deprotection of the hydroxyl represented by X, if appropriate, converting the resulting product to one of its salts, if desired.

The quaternary ammonium salts which may be formed with nitrogen (b) of the piperidine when

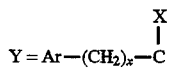

are prepared by reacting the free bases of the compounds (I), in which any other amine groups present are N-protected by a customary N-protecting group, with an excess of an alkylating agent of the formula

A-Q' in which A is a leaving group and is as defined above for (I), preferably a chloride or an iodide, and Q' is as defined above for (I), and the reaction mixture is heated in a solvent selected for example from methylene chloride, chloroform, acetone or acetonitrile, at a temperature between room temperature and the reflux point, for one to several hours, to give a mixture of the axial and equatorial diastereoisomers of the quaternary ammonium salts after treatment by the customary methods and after deprotection if appropriate.

A is preferably an iodide, which can be exchanged with another anion or with a pharmacologically acceptable anion, for example a chloride, by elution of the compound (I) on an ion exchange resin, for example Amberlite IRA68® or Duolite A375®.

The diastereoisomers are separated by the customary methods, for example by chromatography or recrystallization.

Each of the axial or equatorial diastereoisomers of the compounds (I), in the form of racemates or in the form of optically pure R or S enantiomers, forms part of the invention.

The N-oxide derivatives which may be formed with nitrogen (b) of the piperidine when

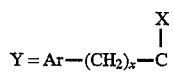

are prepared by reaction with a peroxide derivative, for example metachloroperbenzoic acid or hydrogen peroxide, by the customary methods.

The functional derivative of the acid (III) used is either the acid itself, suitably activated for example by cyclohexylcarbodiimide or by benzotriazolyl-N-oxytrisdimethylaminophosphonium hexafluorophosphate (BOP), or else one of the functional derivatives which react with amines, for example an anhydride, a mixed anhydride, the acid chloride or an activated ester.

When the starting material used is a compound of formula (II) in which E is a group

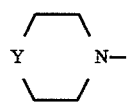

the method of the present invention can be represented and illustrated in detail by scheme 1 below:

(II') with BOP and then to add the acid (III) in the presence of an organic base such as, for example, triethylamine, in a solvent such as methylene chloride or dimethylformamide, at room temperature. The compounds (I) obtained are isolated and purified by the customary methods such as, for example, chromatography or recrystallization.

When the starting material used is a compound of formula (II) in which E is a tetrahydropyranyloxy group (THP-O-), the method of the present invention can be represented and illustrated by scheme 2.

The reactions of the compound (II) with the reactants (IIIa) and (IV) take place as described above for scheme 1, it being possible for the acid chloride (IIIa) to be replaced with a different functional derivative or with the free acid activated for example by BOP.

The intermediate (V) obtained in this way is deprotected by mild acid hydrolysis to give the free hydroxylated compound (VI), from which the mesylate (VII) is prepared in order to substitute it with a secondary amine of formula (VIII) in the final step to give the compounds (I) according to the invention.

SCHEME 1

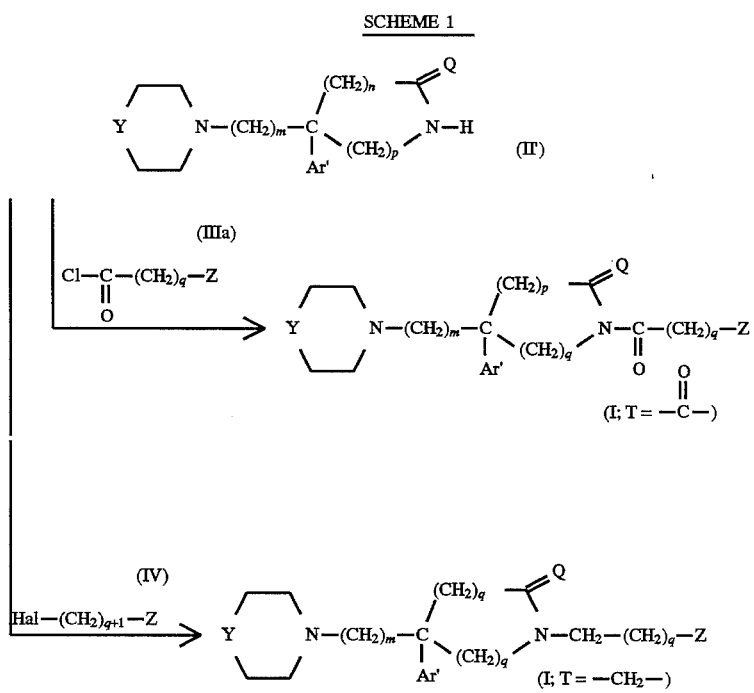

In formula (IIIa) above, the acid chloride is considered as a reactive functional derivative of the acid (III). It is possible, however, to use a different functional derivative or to start from the free acid (III), the procedure being to couple

SCHEME 2

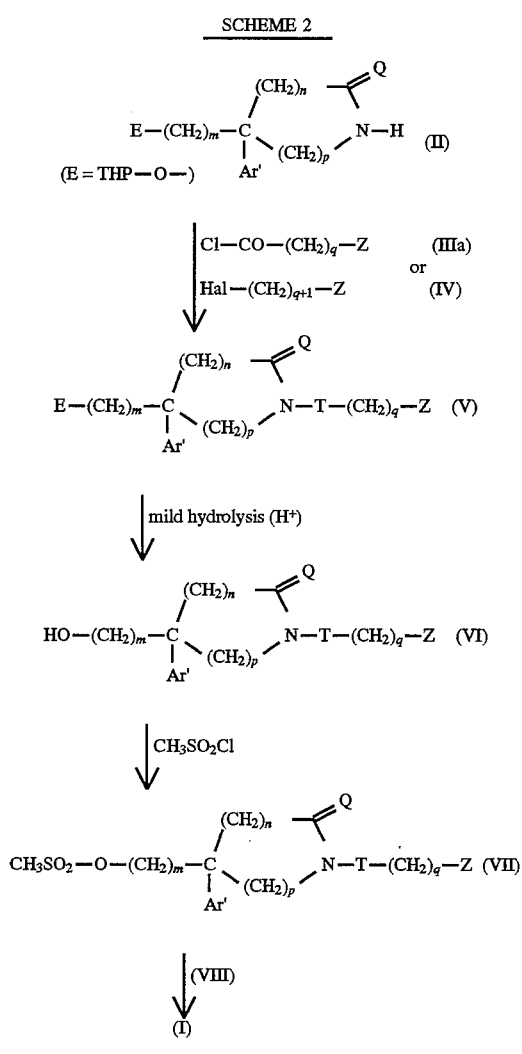

The products of formula (I) obtained in this way are isolated, in the form of the free base or a salt, by the conventional techniques.

When the compound of formula (I) is obtained in the form of the free base, a salt is formed by treatment with the chosen acid in an organic solvent. Treatment of the free base, dissolved for example in an alcohol such as isopropanol, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, oxalate, maleate, fumarate and naphthalene-2-sulfonate, for example, are prepared in this way.

When the reaction is complete, the compounds of formula (I) can be isolated in the form of one of their salts, for example the hydrochloride or oxalate; in this case, if necessary, the free base can be prepared by neutralization of said salt with a mineral or organic base such as sodium hydroxide or triethylamine, or with an alkali metal carbonate or bicarbonate such as sodium or potassium carbonate or bicarbonate.

Starting from the free bases, it is also possible to prepare the quaternary ammonium salts by reaction with an alkylating agent, or the N-oxide derivatives, on nitrogen (b) of the piperidine, it being understood that any other amine groups present on (I) are N-protected by N-protecting groups which are well known to those skilled in the art.

The starting compounds of formula (II) are prepared from commercially available nitriles or prepared by known methods according to the schemes below.

When n is equal to zero, the compound (II) is prepared by the method of D. C. Bishop et al., J. Med. Chem., 1968, 11, 466–470, according to scheme 3 below:

SCHEME 3

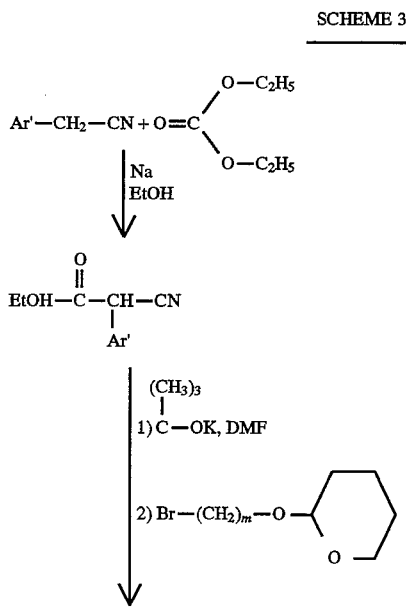

-continued
SCHEME 3
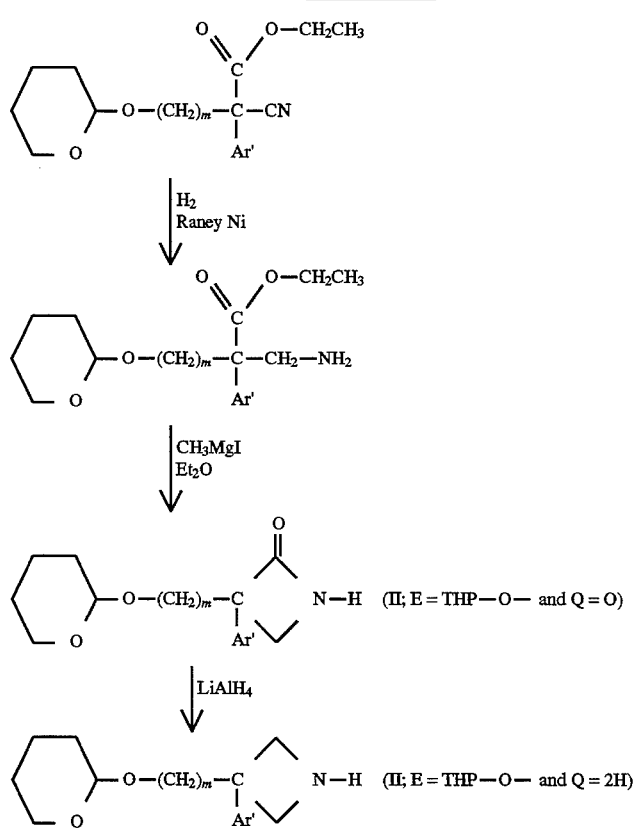
When n=1, 2 or 3, the corresponding compounds (II) are prepared according to scheme 4 below:
SCHEME 4
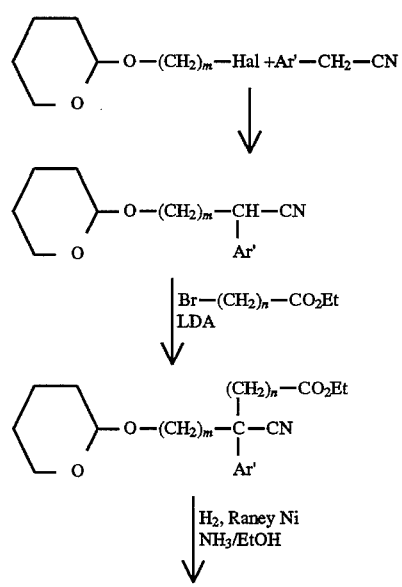

-continued
SCHEME 4

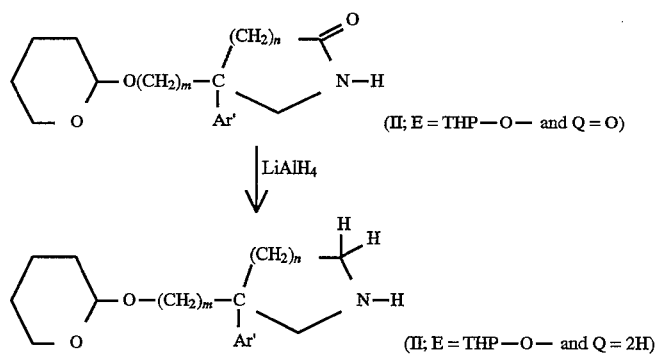

When p=2, then n=1, Q=2H and m=2 and the intermediate (II) is prepared by the method of H. Bochow et al., Chem. Ber., 1975, 108, 3475–3482. The preparation is illustrated by scheme 5 below:

SCHEME 5

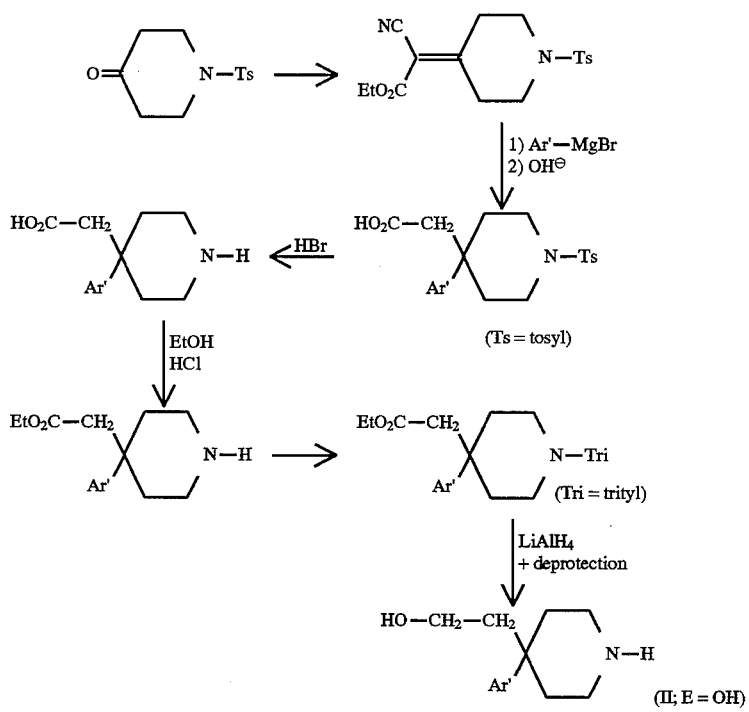

The OH and NH groups may or may not be protected by conventional O-protecting or N-protecting groups which are well known to those skilled in the art.

The enantiomers of formula (I*)

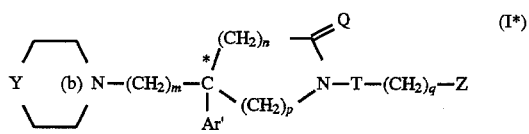

in which:

"*" means that the carbon atom marked with this symbol has a determined (+) or (−) absolute configuration, and Y, m, Ar', n, p, Q, T, q and Z are as defined above for the derivatives of formula (I) or one of their salts with mineral or organic acids, or, with nitrogen atom (b), one of their quaternary ammonium salts or an N-oxide derivative, can be isolated by resolution of the racemic mixtures (I).

The salts or derivatives of the enantiomers (I*) are prepared as defined above for the salts and derivatives of the compounds of formula (I).

The enantiomers (I*) are novel compounds forming part of the invention.

It is also possible to resolve racemic mixtures of the products of formula (II) in which m, Ar', n and p are as defined for (I), E is a hydroxyl and Q is hydrogen, in order to prepare the enantiomers (I*) of the products of formula (I).

The resolution of the racemates is carried out on the intermediates (II) which are capable of giving salts with optically active acids. The enantiomers are then separated by the conventional methods such as crystallization or chiral preparative high-pressure chromatography.

The optically pure amino alcohol prepared in this way is a novel compound forming part of the invention and has the formula

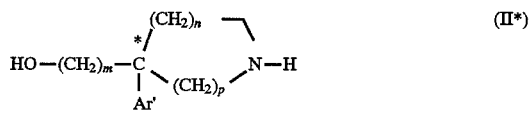
(II*)

in which "*" means that the carbon atom marked with this symbol has a determined (+) or (−) configuration.

The optically pure intermediates of formulae (V) and (VI) are novel products of particular value and represent a further feature of the present invention. These products can be brought together under the following formula:

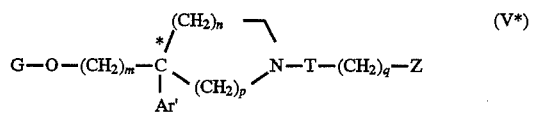
(V*)

in which:

"*", m Ar', n, p, T q and Z are as defined above and G is hydrogen, a tetrahydropyran-2-yl group or a methanesulfonyl group.

The racemic mixtures of the compounds (II) are prepared as indicated in schemes 3, 4 and 5 above.

The optically pure compounds (V*) are prepared according to the reaction sequence indicated in scheme 2 above, starting from the optically pure compounds (II), i.e. (II*), to give the final products according to the invention in optically pure form, i.e. (I*).

When the substituent $-(CH_2)_q-Z$ is a benzyl group substituted on the $-CH-$ by a hydroxyl, an alkoxy or a $C_1-C_4$ alkyl, a mixture of either two or four diastereoisomers is obtained according to whether an optically pure or optically impure α-substituted benzyl derivative is reacted with an optically pure or optically impure amine derivative.

These diastereoisomers form part of the invention.

The compounds according to the invention were subjected to biochemical tests.

The compounds (I) and their salts showed antagonistic properties towards the binding of substance P in tests performed on rat cortical membranes and IM9 lymphoblasts, according to M. A. Cascieri et al., J. Biol. Chem., 1983, 258, 5158–5164, and D. D. Paya et al., J. Immunol., 1984, 133, 3260–3265.

The same compounds and their salts showed antagonistic properties towards the binding of NKA in tests performed on rat duodenal membranes, according to L. Bergstom et al., Mol. Pharmacol., 1987, 32, 764–771.

The same compounds and their salts showed antagonistic properties towards the binding of eledoisin in tests performed on rat membranes, according to A. C. Foster et al., Br. J. Pharmacol., 1988, 94, 602–608.

Eledoisin is a peptide of batrachian origin which is equivalent to neurokinin B.

The compounds according to the invention are antagonistic towards substance P, neurokinin A or neurokinin B.

Thus compound 2 of Example 2 antagonizes the binding of substance P with a Ki of 8.3 nanomolar, compound 7 of Example 7 antagonizes the binding of neurokinin A with a Ki of 1.3 nanomolar and compound 3 of Example 3 antagonizes the binding of eledoisin with a Ki of 200 nanomolar.

The compounds of the present invention are generally administered in dosage units. Said dosage units are preferably formulated as pharmaceutical compositions in which the active principle is mixed with a pharmaceutical excipient.

Thus, according to another feature, the present invention relates to pharmaceutical compositions containing, as the active principle, a compound of formula (I) or one of its pharmaceutically acceptable salts.

The compounds of formula (I) above and their pharmaceutically acceptable salts can be used at daily doses of 0.01 to 100 mg per kilogram of body weight of the mammal to be treated, preferably at daily doses of 0.1 to 50 mg/kg. In humans the dose can preferably vary from 0.5 to 4000 mg per day, more particularly from 2.5 to 1000 mg, depending on the age of the subject to be treated or the type of treatment: prophylactic or curative.

In the pharmaceutical compositions of the present invention for oral, sublingual, subcutaneous, intramuscular, intravenous, transdermal, local or rectal administration, the active principles can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, subcutaneous, intramuscular, intravenous, intranasal or intraocular forms of administration and rectal forms of administration.

When a solid composition in the form of tablets is prepared, the main active principle is mixed with a pharmaceutical vehicle such as gelatin, starch, lactose, magnesium stearate, talc, gum arabic or the like. The tablets can be coated with sucrose or other appropriate substances or they can be treated so as to have a prolonged or delayed activity and so as to release a predetermined amount of active principle continuously.

A preparation in the form of gelatin capsules is obtained by mixing the active principle with a diluent and pouring the mixture obtained into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible granules or powders can contain the active principle mixed with dispersants or wetting agents, or suspending agents such as polyvinylpyrrolidone, as well as with sweeteners or taste correctors.

For rectal administration, suppositories are used which are prepared with binders melting at the rectal temperature, for example cacao butter or polyethylene glycols.

For parenteral, intranasal or intraocular administration, aqueous suspensions, isotonic saline solutions or sterile and injectable solutions are used which contain pharmacologically compatible dispersants and/or wetting agents, for example propylene glycol or butylene glycol.

For administration by inhalation, an aerosol is used which contains for example sorbitan trioleate or oleic acid, as well as trichlorofluoromethane, dichlorofluoromethane, dichlorotetrafluoroethane or any other biologically compatible propellant gas.

The active principle can also be formulated as microcapsules, with one or more carriers or additives if appropriate.

The above-mentioned compositions can also contain other active products such as, for example, bronchodilators, antitussives or antihistamines.

The following Examples illustrate the invention without however implying a limitation.

The melting or decomposition points of the products, m.p., were measured on a Koffler heating bench. The $^{13}C$ nuclear magnetic resonance spectra were run at 50 MHz in dimethyl sulfoxide.

EXAMPLE 1

5-[2-(4-Benzylpiperidin-1-yl)ethyl]-5-(3,4-dichlorophenyl)-1-benzylpiperidinone hydrochloride (I): Y–N–=⟨phenyl⟩–CH$_2$–⟨piperidine⟩–N–;

m = 2; n = 2; p = 1; Q = O; Ar′ = –⟨3,4-dichlorophenyl⟩

–T–(CH$_2$)$_q$–Z = –CH$_2$–⟨phenyl⟩

A) 3,4-Dichlorotetrahydropyranyloxyethyl-α-benzeneacetonitrile 20 g of a 55–60% dispersion of sodium hydride in oil are suspended in 200 ml of dry tetrahydrofuran. A solution of 85 g of 3,4-dichlorophenylacetonitrile in 500 ml of tetrahydrofuran is added dropwise at 20° C. over 30 minutes and the reaction mixture is then stirred at room temperature for 2 hours. The mixture is cooled to −20° C., a solution of 98 g of 2-bromoethoxytetrahydropyran in 100 ml of tetrahydrofuran is added, the mixture is allowed to return to room temperature and, after 2 hours, a solution of 50 g of ammonium chloride in 3 liters of water is added. Extraction is carried out with 1.5 liters of ether and the extract is washed with a saturated solution of sodium chloride, decanted, dried over MgSO$_4$ and concentrated under vacuum.

The residue is chromatographed on silica gel using methylene chloride as the eluent. The pure product fractions are concentrated under vacuum to give 83.6 g of an oil.

B) Ethyl γ-tetrahydropyranyloxyethyl-γ-cyano-3,4-dichlorobenzylbutanoate 21 g of the nitrile prepared above according to A) are dissolved in 100 ml of tetrahydrofuran, a solution of 0.067 mol of lithium diisopropylamide in 100 ml of tetrahydrofuran is then added dropwise at room temperature and the reaction mixture is stirred for one hour at room temperature. 12 g of ethyl bromopropionate are then added and the mixture is heated at 50° C. for two hours. It is cooled, poured into a saturated solution of ammonium chloride and extracted with ether, the extract is washed with water and the ether phase is separated off by decantation, dried over Na$_2$SO$_4$ and concentrated under vacuum. The residue is purified by chromatography on silica gel using methylene chloride/ethyl acetate 100/1 (v/v) as the eluent. Concentration of the pure fractions gives 13 g of the expected compound.

C) 5-Tetrahydropyranyloxyethyl-5-(3,4-dichlorophenyl)piperidinone 13 g of the compound prepared above are dissolved in 250 ml of ethanol and 40 ml of aqueous amonia and hydrogenated at room temperature and atmospheric pressure in the presence of Raney nickel. When the theoretical volume of hydrogen has been absorbed, the mixture is filtered on Célite and the filtrate is concentrated under vacuum. The residue is taken up in water and extracted with ether end the ether phase is then washed with water, dried over MgSO$_4$ and concentrated under vacuum.

m=9 g.

D) 5-Tetrahydropyranyloxyethyl-5-(3,4-dichlorophenyl)-1-benzylpiperidinone 2.05 g of benzyl bromide are added to a solution of 4.5 g of the product prepared above in 60 ml of dimethylformamide, in the presence of 0.3 g of sodium hydride. The reaction mixture is heated at 40°–50° C. for two hours and concentrated under vacuum. The residue is taken up in water and extracted with ether and the ether phase is washed with water, dried over MgSO$_2$ and concentrated under vacuum. The residue is chromatographed on silica gel using methylene chloride/methanol 100/1 (v/v) as the eluent.

The pure product fractions are concentrated under vacuum.

m=2 g.

E) 5-Methanesulfonyloxyethyl-5-(3,4-dichlorophenyl)-1-benzylpiperidinone 2 g of the product prepared above are dissolved in 40 ml of methanol saturated with gaseous hydrochloric acid and the solution is stirred for two hours at room temperature. The solvents are concentrated under vacuum, the residue is taken up in a 50/50 pentane/ether mixture and the precipitate is then filtered off. The precipitate is dissolved in 50 ml of methylene chloride, 0.4 g of triethylamine and 0.45 g of mesyl chloride are added and the mixture is stirred for half an hour at room temperature. It is concentrated under vacuum, the residue is taken up in water and extracted with ether and the ether phase is washed with water, decanted, dried over MgSO$_4$ and concentrated under vacuum.

m=1.6 g.

F) Compound 1

0.68 g of the product prepared above and 0.63 g of 4-benzylpiperidine are dissolved in 2 ml of dimethylformamide and the mixture is heated at 80° C. for two hours. The solution is cooled, poured into water and extracted with ethyl acetate and the organic phase is decanted, dried over MgSO$_4$ and concentrated under vacuum. The residue is purified by chromatography on silica gel using methylene chloride/methanol 100/3 (v/v) as the eluent.

The pure product fractions are concentrated under vacuum and this is followed by preparation of the hydrochloride, which is solidified in a 50/50 ether/pentane mixture.

m=0.25 g.

M.p.=115° C.

EXAMPLE 2

3-[2-(4-Benzylpiperidin-1-yl)ethyl]-3-(3,4-dichlorophenyl)-1-phenylacetylpiperidine hydrochloride (I): Y–N–=⟨phenyl⟩–CH$_2$–⟨piperidine⟩–N–;

m = 2; n = 2; p = 1; Q = 2H; Ar′ = –⟨3,4-dichlorophenyl⟩

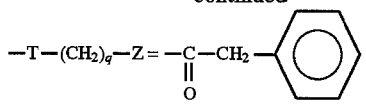

A) 3-Tetrahydropyranyloxyethyl-3-(3,4-dichlorophenyl) piperidine 4.5 g of 5-tetrahydropyranyloxyethyl-5-(3,4-dichlorophenyl)piperidinone prepared according to Example 1 C) are dissolved in 50 ml of tetrahydrofuran and the solution is added to a suspension of 0.9 g of lithium aluminum hydride, heated to 60° C. The reaction mixture is heated for one hour at 60° C. and then cooled. 1 ml of water, 1 ml of 4 N sodium hydroxide and 3 ml of water are added. The inorganic material is filtered off and the filtrate is concentrated under vacuum. The residue is taken up in ether, dried over MgSO$_4$ and concentrated under vacuum to give 3.5 g of the expected product.

B) 3-Tetrahydropyranyloxyethyl-3-(3,4-dichlorophenyl)-1-phenylacetylpiperidine 0.75 g of phenylacetyl chloride is added to a solution of 1.7 g of the product prepared above and 0.9 g of triethylamine in 50 ml of methylene chloride. The reaction mixture is stirred for one hour at room temperature and concentrated under vacuum. The residue is taken up in ethyl acetate and then washed with water and the organic phase is dried over MgSO$_4$ and concentrated under vacuum. The residue is purified by chromatography on silica gel using methylene chloride/methanol 100/0.5 (v/v) as the eluent.

Concentration of the pure fractions gives 1 g of the expected product.

C) 3-Methanesulfonyloxyethyl-3-(3,4-dichlorophenyl)-1-phenylacetylpiperidine 0.8 g of the product obtained above is dissolved in 40 ml of methanol saturated with hydrochloric acid and the mixture is stirred for half an hour at room temperature. It is concentrated under vacuum and the residue is taken up in 40 ml of methylene chloride. 0.4 g of triethylamine and 0.23 g of mesyl chloride are added and the reaction mixture is stirred for one hour at room temperature and then concentrated under vacuum. The residue is taken up in ethyl acetate and washed with water and the organic phase is separated off by decantation, dried over MgSO$_4$ and concentrated under vacuum.

m=0.71 g.

D) Compound 2

0.7 g of the product prepared above and 0.52 g of 4-benzylpiperidine dissolved in 2 ml of dimethylformamide are heated at 80° C for three hours. The reaction mixture is cooled, poured into water and extracted with ether, the ether phase is washed with water, dried over MgSO$_4$ and concentrated under vacuum and the hydrochloride is then recrystallized from a methylene chloride/ether mixture.

m=0.12 g.

M.p.=210°–212° C.

Compounds 3 to 6 described in Table I below are prepared by following the procedure of Example 1.

TABLE I

TABLE I-continued

[Structure: Y-N-(morpholine ring)-N-(CH₂)₂-C with (CH₂)ₙ branch, attached to 3,4-dichlorophenyl group, connected to N-T-(CH₂)q-Z with C=O]

| Example n° | Y⟨N-⟩ | n | —T—(CH₂)q—Z | M.p.; °C. Salt |
|---|---|---|---|---|
| 6 | [phenyl-C(OH)-piperidine]-N— | 2 | —CH₂—[phenyl-O—CH₃] | 136 HCl |

Compounds 7 to 15 described in Table II below are prepared by following the procedure of Example 2.

TABLE II

[Structure: Y-N-(morpholine ring)-N-(CH₂)₂-C with (CH₂)ₙ branch, attached to 3,4-dichlorophenyl group, connected to N-T-(CH₂)q-Z]

| Example n° | Y⟨N-⟩ | n | —T—(CH₂)q—Z | M.p.; °C. Salt |
|---|---|---|---|---|
| 7 | [phenyl-C(OH)-piperidine]-N— | 1 | —C(=O)—[phenyl] | 139 HCl |
| 8 | [phenyl-CH₂-piperidine]-N— | 1 | —C(=O)—CH₂—[phenyl] | 112 HCl |
| 9 | [phenyl-C(OH)-piperidine]-N— | 2 | —C(=O)—[phenyl] | 160 HCl |
| 10 | [phenyl-C(O-C(=O)-CH₃)-piperidine]-N— | 2 | —C(=O)—[phenyl] | 142 HCl |

TABLE II-continued

[Structure: Y-N(morpholine-like ring)-(CH₂)₂-C with (CH₂)ₙ branch, attached to 3,4-dichlorophenyl, and CH₂-N-T-(CH₂)q-Z]

| Example n° | Y\[N-\] | n | —T—(CH₂)q—Z | M.p.; °C. Salt |
|---|---|---|---|---|
| 11 | phenyl-CH₂-piperidin-4-yl-N— | 2 | —C(=O)—CH₂—(3,5-difluorophenyl) | 114 HCl |
| 12 | phenyl-CH₂-piperidin-4-yl-N— | 2 | —C(=O)—(4-fluoronaphth-1-yl) | 168 HCl |
| 13 | phenyl-CH₂-piperidin-4-yl-N— | 2 | —C(=O)—CH₂—(3-OC₂H₅-phenyl) | 102 HCl |
| 14 | phenyl-CH₂-piperidin-4-yl-N— | 2 | —C(=O)—CH₂—(3-OiPr-phenyl) | 169 HCl |
| 15 | phenyl-CH₂-piperidin-4-yl-N— | 2 | —C(=O)—CH₂—(3,5-dimethoxyphenyl) | 110 HCl | iPr = isopropyl

Compounds 16 to 19 described in Table III below are obtained by following the procedure of Examples 1 and 2 above, replacing the 3,4-dichlorophenylacetonitrile with α-naphthylacetonitrile.

TABLE III

| Example n° | 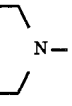 | Q | —T—(CH$_2$)$_q$—Z | M.p.; °C. Salt |
|---|---|---|---|---|
| 16 | 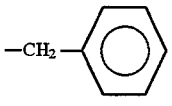 | O |  | 104 HCl |
| 17 | 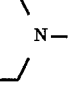 | H | 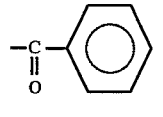 | 115 HCl |
| 18 |  | H | 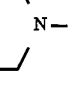 | 105 HCl |
| 19 | 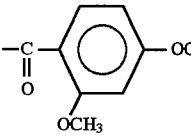 | H | 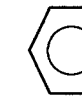 | 110 HCl |

EXAMPLE 20

3-[2-(4-Benzylpiperidin-1-yl)ethyl]-3-(3,4-dichlorophenyl)-1-(3-isopropoxyphenyl)acetylazepine hydrochloride

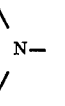

m = 2; n = 3; p = 1; Q = 2H; Ar' = 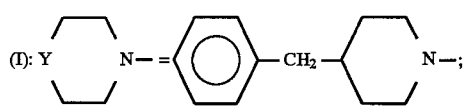

—T—(CH$_2$)$_q$—Z = —CH$_2$— 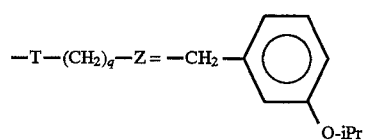

A) Ethyl δ-tetrahydropyranyloxyethyl-δ-cyano-3,4-dichlorobenzylpentanoate 4.6 g of 60% NaH are added in small portions to 36 g of 3,4-dichloro-α-tetrahydropyranyloxyethylbenzeneacetonitrile (prepared according to step A of Example 1) dissolved in 100 ml of dimethylformamide. The reaction mixture is stirred for 3 hours at room temperature and cooled to 0° C. and 22.4 g of ethyl 4-bromobutyrate in 40 ml of dimethylformamide are then added. The reaction mixture is stirred for 3 hours at room temperature, poured into water and extracted with ether and the extract is washed with a saturated solution of NaCl, dried over Na$_2$SO$_4$ and concentrated under vacuum. The residue obtained is purified by chromatography on silica gel using toluene as the eluent.

m=24 g.

B) 6-Tetrahydropyranyloxyethyl-6-(3,4-dichlorophenyl) azepinone

A solution of 8 g of the product obtained above in 120 ml of ethanol is hydrogenated at atmospheric pressure and room temperature in the presence of Raney nickel.

When the theoretical volume of hydrogen has been consumed, the catalyst is filtered off and the filtrate is concentrated under vacuum.

The oil obtained is then taken up in 20 ml of xylene and the reaction mixture is refluxed for 48 hours. It is evaporated and the residue obtained is purified by chromatography on silica gel using methylene chloride/methanol 100/1 (v/v) as the eluent.

This gives 4 g of an oil.

C) 3-Tetrahydropyranyloxyethyl-3-(3,4-dichlorophenyl) azepine 1.7 g of the expected product are obtained in the form of an oil from 2 g of the product obtained above and 0.49 g of lithium aluminum hydride by following the procedure of Example 2, step A.

D) 3-Tetrahydropyranyloxyethyl-3-(3,4-dichlorophenyl)-1-(3-isopropoxyphenyl) acetylazepine 1.7 g of the expected product are obtained from 1.7 g of the product obtained above by following the procedure of Example 2, step B.

E) 3-Methanesulfonyloxyethyl-3-(3,4-dichlorophenyl)-1-(3-isopropoxyphenyl) acetylazepine 1.5 g of the expected product are obtained from 1.7 g of the product obtained above and 0.34 g of mesyl chloride by following the procedure of Example 2, step C.

F) Compound 20

1.5 g of the product obtained above and 1.4 g of 4-benzylpiperidine dissolved in 3 ml of dimethylformamide are heated at 80° C. for 2 hours. The reaction mixture is cooled, poured into water and extracted with ether and the organic phase is washed with water, dried over Na₂SO₄ and concentrated under vacuum.

The residue obtained in this way is purified by chromatography on silica gel using CH₂Cl₂/CH₃OH 100/2 (v/v) as the eluent. The pure fractions are concentrated and the hydrochloride is prepared in isopropyl ether, filtered off, washed with ether and dried under vacuum to give 1.3 g of the expected product.

M.p.=164° C.

EXAMPLE 21

3-[2-(4-Benzylpiperidin-1-yl)ethyl]-3-(3,4-dichlorophenyl)-1-(3-methoxyphenyl)acetylazetidine hydrochloride

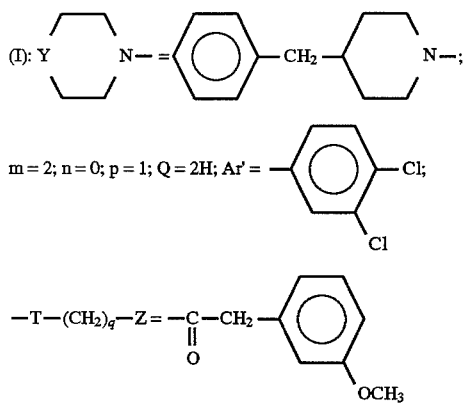

The above compound was prepared according to scheme 3 of the description.

A) 3-Tetrahydropyranyloxyethyl-3-(3,4-dichlorophenyl)-1-(3-methoxyphenyl)acetylazetidine 1.5 g of BOP are added to a solution of 1 g of 3-tetrahydropyranyloxyethyl-3-(3,4-dichlorophenyl) azetidine in 50 ml of methylene chloride, in the presence of 1 g of triethylamine and 0.5 g of 3-methoxyphenylacetic acid. The reaction mixture is stirred for hour at room temperature and evaporated to dryness and the residue is taken up in ethyl acetate and washed with water, dilute sodium hydroxide solution, a buffer of pH 2 and finally a saturated aqueous solution of NaCl. The organic phase is dried over MgSO₄ and evaporated to dryness. The residue is purified by chromatography on silica gel using CH₂Cl₂/CH₃OH 100/0.75 (v/v) as the eluent.

This gives 0.50 g of an oil.

B) 3-Methanesulfonyloxyethyl-3-(3,4-dichlorophenyl)-1-(3-methoxyphenyl)acetylazetidine Ether saturated with hydrochloric acid is added to a solution of 0.50 g of the product prepared above in 50 ml of methanol until the pH is 1. The solution is stirred at room temperature for 1 hour and evaporated to dryness, the residue is taken up in water and extracted with AcOEt and the extract is washed with water, dried over MgSO₄ and evaporated to dryness.

The oil obtained is taken up in 30 ml of methylene chloride, and 0.20 g of triethylamine and 0.12 g of mesyl chloride are added. The reaction mixture is stirred at room temperature for 1 hour and evaporated to dryness and the residue is taken up in ethyl acetate, washed with water, dried over MgSO₄ and evaporated to dryness.

This gives 0.50 g of an oil.

C) Compound 21

A solution of 0.50 g of the product described above in 2 ml of dimethylformamide, with 0.40 g of 4-benzylpiperidine, is heated at 80° C. for 3 hours. The reaction mixture is cooled, poured into water and extracted with ethyl acetate and the extract is washed with water, dried over MgSO₄ and evaporated to dryness.

The residue obtained in this way is purified by chromatography on silica gel using CH₂Cl₂/CH₃OH 100/2.5 (v/v) as the eluent.

The pure fractions are concentrated under vacuum and the hydrochloride is prepared by the addition of ether saturated with hydrochloric acid. The residue is taken up in methylene chloride and the hydrochloride is precipitated in ether, filtered off, washed with ether and dried under vacuum.

This gives 0.22 g of the expected product.

M.p.=102° C.

EXAMPLE 22

4-[2-(4-Benzylpiperidin-1-yl)ethyl]-4-(3-methylphenyl)-1-(3-chlorophenyl)acetylpiperidine hydrochloride

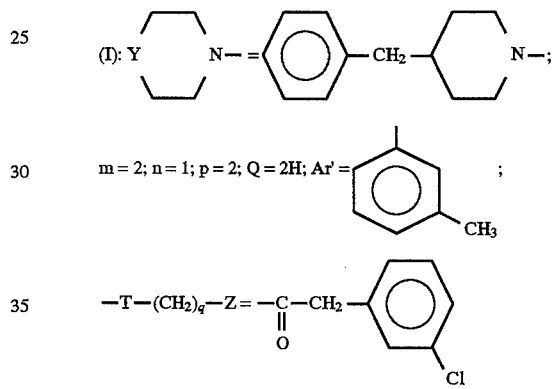

The above compound is prepared according to scheme 5 of the description.

A) 4-Methanesulfonyloxyethyl-4-(3-methylphenyl)-N-tritylpiperidine 3.8 ml of methanesulfonyl chloride are added dropwise to 21 g of 4-(2-hydroxyethyl)-4-(3-methyl-phenyl)-N-tritylpiperidine (prepared according to scheme 5) dissolved in 200 ml of methylene chloride, cooled to 0° C. The reaction mixture is left for half an hour at room temperature, washed twice with water, dried over MgSO₄ and concentrated under vacuum.

This gives 23.5 g of a foam.

B) 4-[2-(4-Benzylpiperidin-1-yl)ethyl]-4-(3-methyl-phenyl)-N-tritylpiperidine

A solution of 18.5 g of the mesylate described above and 13.5 g of 4-benzylpiperidine in 40 ml of dimethylformamide is heated for 4 hours at 60° C. The reaction mixture is poured into 500 ml of iced water and the precipitate is filtered off and rinsed with water. The precipitate is taken up in ether, washed with dilute NaOH and then water, dried over MgSO₄ and concentrated to dryness.

The residue obtained is purified by chromatography on silica gel using CH₂Cl₂/CH₃OH 100/3 (v/v) as the eluent.

This gives 18 g of a foam.

C) 4-[2-(4-Benzylpiperidin-1-yl)ethyl]-4-(3-methyl-phenyl) piperidine dihydrochloride A solution of 18 g of the above product in 150 ml of 50% formic acid is heated at 60° C. for 30 minutes. It is cooled, the triphenylcarbinol is filtered off and rinsed with water and the filtrate is concentrated to dryness. The residue is taken up in water, washed with ether, rendered alkaline with a solution of NaOH and extracted with methylene chloride and the extract is dried over MgSO$_4$ and concentrated to dryness.

The base is dissolved in methylene chloride, ether saturated with hydrochloric acid is added and the mixture is concentrated to dryness. The hydrochloride prepared in this way is stirred in ether, filtered off and dried.

m=12.7 g.
M.p.=160° C.

D) Compound 22

2.4 g of BOP are added to a solution of 2 g of the product prepared above in 30 ml of methylene chloride, with 0.77 g of 3-chlorophenylacetic acid and 2.2 g of triethylamine. The reaction mixture is stirred for 30 minutes at room temperature and concentrated to dryness and the residue is taken up in ethyl acetate, washed with water, then a dilute solution of NaOH and then a saturated aqueous solution of NaCl, dried over MgSO$_4$ and concentrated under vacuum. The residue is purified by chromatography on silica gel using CH$_2$Cl$_2$/CH$_3$OH 100/10 (v/v) as the eluent. The hydrochloride is prepared by the addition of ether saturated with hydrochloric acid and the mixture is concentrated to dryness. The residue is taken up in isopropyl ether, filtered off and dried under vacuum.

m=2.1 g.
M.p.=106° C.

The compounds described in Table IV below are prepared by following the procedure indicated above in Example 22.

EXAMPLE 26

3-[3-(4-Benzylpiperidin-1-yl)propyl]-3-(3,4-dichlorophenyl)-1-(3-methoyphenyl)acetylpiperidine hydrochloride

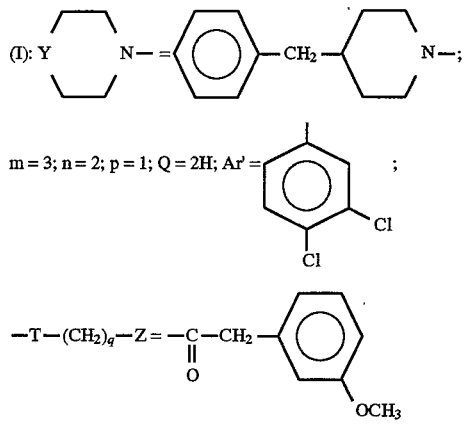

A) 3,4-Dichlorotetrahydropyranyloxypropyl-α-benzeneacetonitrile 35 g of the expected product are obtained in an identical manner to step A of Example 1, starting from 37.2 g of 3,4-dichlorophenylacetonitrile and 44.6 g of 3-bromopropoxytetrahydropyran.

B) Ethyl γ-tetrahydropyranyloxypropyl-γ-cyano-3,4-dichlorobenzylbutanoate

TABLE IV

| Example n° | Y N— | —(CH$_2$)$_q$—Z | M.p.; °C. |
|---|---|---|---|
| 23 | phenyl-CH$_2$-piperidin-N— | —CH$_2$-(3,5-dimethoxyphenyl with OCH$_3$, OCH$_3$) | 105 |
| 24 | phenyl-CH$_2$-piperidin-N— | 3,4-dimethoxyphenyl (OCH$_3$, OCH$_3$) | 146 |
| 25 | phenyl(OH)-piperidin-N— | phenyl | 143 |

28 g of the expected product are obtained from 35 g of the product obtained above and 19.2 g of ethyl bromopropionate by following an identical procedure to step B of Example 1.

C) 5-Tetrahydropyranyloxypropyl-5-(3,4-dichlorophenyl)piperidone

A solution of 23 g of the product obtained above in 650 ml of ethanol is hydrogenated at atmospheric pressure and room temperature in the presence of Raney nickel. When the theoretical volume of hydrogen has been consumed, the catalyst is filtered off, the filtrate is evaporated to dryness and the residue is taken up in ether, washed with water and a buffer of pH 2, dried over $Na_2SO_4$ and evaporated to dryness.

This gives 18 g of the expected product.

D) 3-Tetrahydropyranyloxypropyl-3-(3,4-dichlorophenyl)piperidine

A solution of 14 g of the product obtained above in 50 ml of tetrahydrofuran is added dropwise to a suspension of 2.75 g of lithium aluminum hydride, heated to 60° C.

The temperature is kept at 60° C. for 1 hour. The reaction mixture is cooled and hydrolyzed by the addition of 3 ml of water, 3 ml of a 4N solution of NaOH and 9 ml of water. The inorganic material is separated off and the organic phase is evaporated under vacuum.

This gives 12.4 g of the expected product.

E) 3-Tetrahydropyranyloxypropyl-3-(3,4-dichlorophenyl)-1-(3-methoyphenyl)acetylpiperidine 3.9 g of BOP are added to a solution of 3 g of the product prepared above, 2.4 g of triethylamine and 1.3 g of 3-methoxyphenylacetic acid in 50 ml of methylene chloride. The reaction mixture is stirred for 1 hour at room temperature and evaporated to dryness and the residue is taken up in AcOEt, washed with water, dried over $Na_2SO_4$ and evaporated to dryness.

The residue obtained in this way is purified by chromatography on silica gel using $CH_2Cl_2/CH_3OH$ 100/2 (v/v) as the eluent.

Concentration of the pure fractions gives 3 g of the expected product.

F) 3-Methanesulfonyloxypropyl-3-(3,4-dichlorophenyl)-1-(3-methoxyphenyl)acetylpiperidine The expected compound is obtained from 3 g of the product prepared above and 0.68 g of mesyl chloride by following the procedure described in step C of Example 2. 2 g of the expected product are obtained after purification by chromatography on silica gel using $CH_2Cl_2/CH_3OH$ 100/1.5 (v/v) as the eluent and concentration of the pure product fractions.

G) Compound 26

A solution of 2 g of the product obtained above and 1.6 g of 4-benzylpiperidine in 3 ml of dimethylformamide is heated for 1 hour at 70° C. The reaction mixture is cooled, poured into water and extracted with ether and the extract is washed with water, dried over $Na_2SO_4$, filtered and concentrated under vacuum.

The residue obtained in this way is purified by chromatography on silica gel using $CH_2Cl_2/CH_3OH$ 100/3 (v/v) as the eluent. The pure fractions are concentrated under vacuum, the residue is taken up in acetone and the hydrochloride is prepared by the addition of ether saturated with hydrochloric acid. The hydrochloride is filtered off, washed with pentane and dried under vacuum over $P_2O_5$.

This gives 1.1 g of the expected product.

M.p.=108° C.

EXAMPLE 27

3-[3-(4-Phenyl-4-acetamidopiperidin-1-yl)propyl]-3-(3,4-dichlorophenyl)-1-benzoylpiperidine hydrochloride

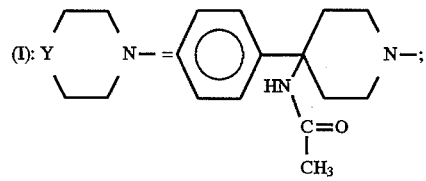

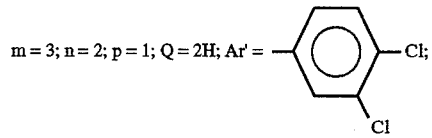

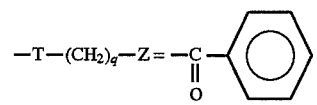

A) 3-Tetrahydropyranyloxypropyl-3-(3,4-dichlorophenyl)-1-benzoylpiperidine 1.13 g of benzoyl chloride are added to 3 g of 3-tetrahydropyranyloxypropyl-3-(3,4-dichlorophenyl)piperidine prepared according to Example 26, step D, in the presence of a solution of 1.62 g of triethylamine in 50 ml of methylene chloride. The reaction mixture is stirred for 30 minutes at room temperature and evaporated to dryness and the residue is taken up in ether, washed with water, dried over $Na_2SO_4$ and evaporated to dryness. The residue obtained in this way is purified by chromatography on silica gel using $CH_2Cl_2/CH_3OH$ 100/1 (v/v) as the eluent.

This gives 3 g of an oil.

B) 3-Methanesulfonyloxypropyl-3-(3,4-dichlorophenyl)-1-benzoylpiperidine

Ether saturated with hydrochloric acid is added to a solution of 3 g of the product prepared above in 50 ml of methanol until the pH is 1. The reaction mixture is stirred for 30 minutes at room temperature and evaporated to dryness. The residue is taken up in 50 ml of methylene chloride and 1.07 g of triethylamine, and 0.72 g of mesyl chloride is then added. The mixture is stirred at room temperature for 1 hour and evaporated to dryness and the residue is taken up in ethyl acetate, washed with water, dried over $Na_2SO_4$, filtered and concentrated under vacuum. The residue is purified by chromatography on silica gel using $CH_2C_2/AcOEt$ 100/3 (v/v) as the eluent.

This gives 1.6 g of the expected product.

C) Compound 27

A solution of 1.5 g of the product prepared above and 1.5 g of 4-phenyl-4-acetamidopiperidine in 5 ml of dimethylformamide is heated at 80° C. for 4 hours. The reaction mixture is cooled, poured into water and extracted with methylene chloride and the extract is washed with water, dried over $Na_2SO_4$, filtered and concentrated under vacuum. The residue is purified by chromatography on silica gel using $CH_2Cl_2/CH_3OH$ 100/5 (v/v) as the eluent. The pure product fractions are concentrated and taken up in methylene chloride, the hydrochloride is prepared by the addition of ether saturated with hydrochloric acid, the mixture is evaporated to dryness and the residue is taken up in ethanol and precipitated in ether. The precipitate is filtered off, washed with pentane and dried under vacuum.

m=0.60 g.

M.p.=184° C.

EXAMPLE 28

5-[3-(4-Hydroxy-4-phenylpiperidin-1-yl)propyl]-5-(3,4-dichlorophenyl)-1-(3-methoxybenzyl)piperidone hydrochloride

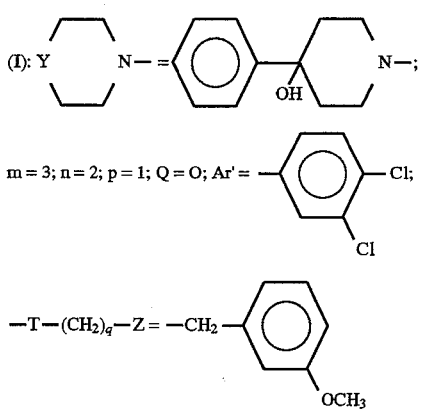

A) 5-Tetrahydropyranyloxypropyl-5-(3,4-dichlorophenyl)-1-(3-methoxybenzyl)piperidone 0.66 g of 60% NaH is added to a solution of 6.4 g of 5-tetrahydropyranyloxypropyl-5-(3,4-dichlorophenyl) piperidone, described in step C of Example 26, in 60 ml of dimethylformamide. The reaction mixture is stirred for 30 minutes at room temperature. 2.5 g of 3-methoxybenzyl chloride are then added dropwise and the reaction mixture is heated for 1 hour at 80° C. The dimethylformamide is evaporated off under vacuum, the residue is extracted with methylene chloride and the extract is washed with water, dried over $Na_4SO_4$ and evaporated to dryness.

The residue obtained in this way is purified by chromatography on silica gel using $CH_2Cl_2$/AcOEt 100/5 (v/v) as the eluent. The pure product fractions are concentrated to give 6 g of an oil.

B) 5-(3-Hydroxypropyl)-5-(3,4-dichlorophenyl)-1-(3-methoxybenzyl)piperidone

A solution of 6 g of the product prepared above in 50 ml of methanol saturated with hydrochloric acid is stirred at room temperature for one hour.

The reaction mixture is evaporated to dryness to give 4.3 g of an oil.

C) 5-Methanesulfonyloxypropyl-5-(3,4-dichlorophenyl)-1-(3-methooxyenzyl)piperidone 1.14 g of mesyl chloride are added to 4.3 g of the product prepared above, in the presence of a solution of 2 g of triethylamine in 50 ml of methylene chloride. The reaction mixture is stirred for 1 hour at room temperature and evaporated to dryness and the residue is taken up in AcOEt, washed with water and a saturated aqueous solution of NaCl, dried over $Na_2SO_4$ and evaporated to dryness.

The residue obtained in this way is purified by chromatography on silica gel using $CH_2Cl_2$/$CH_3OH$ 100/2 (v/v) as the eluent. The pure product fractions are concentrated to give 4 g of an oil.

D) Compound 28

A solution of 4 g of the product prepared above and 3.1 g of 4-hydroxy-4-phenylpiperidine in 5 ml of dimethylformamide is heated at 80° C. for 2 hours. It is cooled, poured into water and extracted with AcOEt and the extract is washed with water, dried over $Na_2SO_4$ and evaporated to dryness. The oil obtained is taken up in ether and the hydrochloride is prepared by the addition of ether saturated with hydrochloric acid. The product is filtered off, washed with ether and dried under vacuum.

m=4 g.
M.p.=110°–117° C.

EXAMPLE 29

3-[3-(4-Hydroxy-4-phenylpiperidin-1-yl)propyl]-3-(3,4-dichlorophenyl)-1-(3-methoxybenzyl)piperidine dihydrochloride

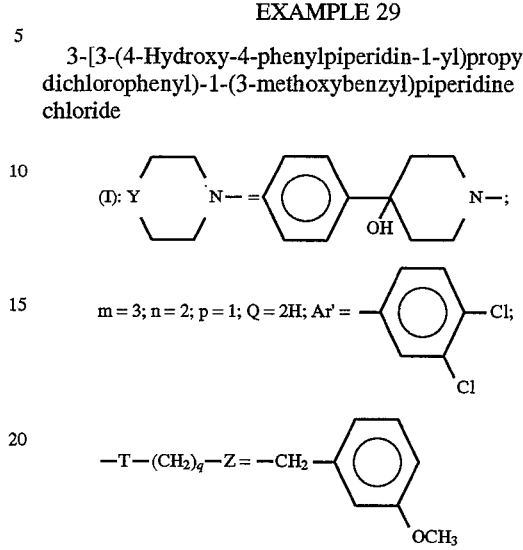

2 g of 5-[3-(4-hydroxy-4-phenylpiperidin-1-yl)-propyl]-5-(3,4-dichlorophenyl)-1 -(3-methoxybenzyl)piperidone are added to a suspension of 0.60 g of lithium aluminum hydride in 50 ml of tetrahydrofuran. The reaction mixture is heated for 1 hour at 60° C., cooled and hydrolyzed with 5 ml of water, the inorganic material is filtered off and the filtrate is evaporated to dryness.

The residue obtained in this way is purified by chromatography on silica gel using $CH_2Cl_2$/$CH_3OH$ 100/5 (v/v) as the eluent, the pure product fractions are concentrated and the hydrochloride is prepared in methylene chloride by the addition of ether saturated with hydrochloric acid.

The hydrochloride is filtered off, washed with ether and dried under vacuum over $P_2O_5$.

m=1.5 g.
M.p.=160°–175° C.

EXAMPLE 30

3-[2-(4-Hydroxy-4-phenylpiperidin-1-yl)ethyl]-3-(3,4-dichlorophenyl)-1-benzylpyrrolidine dihydrochloride

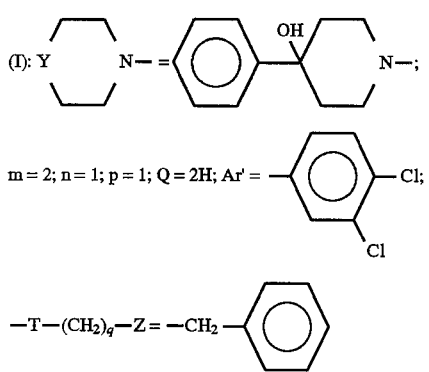

The expected product is obtained by following the procedure of Example 29, starting from the product described in Example 5.

M.p.=170° C.

EXAMPLE 31

3-[2-(4-Benzylpiperidin-1-yl)ethyl]-3-(naphth-1-yl)-1-benzylpiperidine dihydrochloride

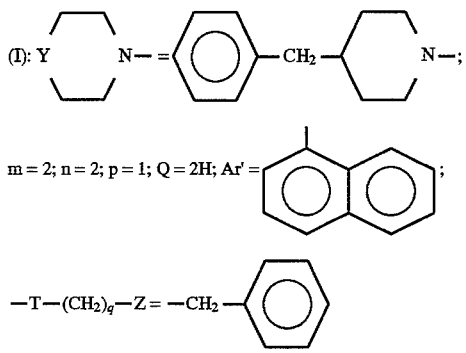

The above compound is obtained by following the procedure of Example 29, starting from the product described in Example 17.

M.p.=140° C.

EXAMPLE 32

3-[2-(4-Benzylpiperidin-1-yl)ethyl]-3-(3,4-dichlorophenyl)-1-(3-isopropoxyphenyl)acetylpiperidine (−) hydrochloride

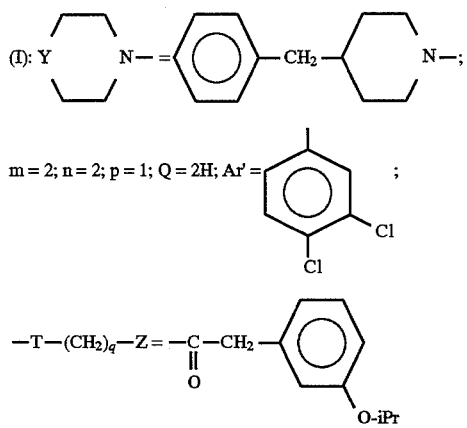

I—PREPARATION OF THE OPTICALLY PURE AMINO ALCOHOL

A) 3-(2-Hydroxyethyl)-3-(3,4-dichlorophenyl)piperidine

A solution of hydrochloric acid in ether is added to a solution of 55 g of 3-tetrahydropyranyloxy-ethyl-3-(3,4-dichlorophenyl)piperidine in 200 ml of methanol until the pH is 1. The mixture is stirred for half an hour at room temperature and concentrated to dryness, the residue is taken up in water, rendered basic with a solution of sodium hydroxide and extracted with methylene chloride and the extract is washed with a saturated solution of NaCl, dried over $Na_2SO_4$ and evaporated to dryness to give an oil.

This is taken up in 200 ml of a 50/50 (v/v) isopropyl ether/ether mixture. The medium is stirred and the product is filtered off, washed with ether and dried under vacuum over $P_2O_5$.

m=45 g.

M.p.=122° C.

B) 3-(2-Hydroxyethyl)-3-(3,4-dichlorophenyl)piperidine (+)

A solution of 23.54 g of L(+)-tartaric acid in 750 ml of 100° ethanol is added to a refluxing solution of 43 g of the product obtained above in 250 ml of 100° ethanol. The reaction mixture is refluxed for half an hour and allowed to return to room temperature and the crystals obtained are filtered off, washed with 100° ethanol and dried under vacuum at 50° C. over $P_2O_5$.

m=31 g.

The product is then recrystallized from 540 ml of 100° ethanol and the crystals are filtered off, washed with ether and dried under vacuum over $P_2O_5$.

m=25 g.

$[\alpha]_D^{20}=+8.5°$ (c=1, $H_2O$).

The tartrate is then taken up in water, neutralized with a solution of NaOH and extracted with methylene chloride and the extract is washed with water, dried over $Na_2SO_4$ and evaporated to dryness. The oil is taken up in an ether/isopropyl ether mixture and the crystals are filtered off, washed with ether and dried under vacuum at 50° C.

m=13.5 g.

M.p.=138° C.

$[\alpha]_D^{20}=+8.2°$ (c=1, $CH_3OH$).

C) 3-(2-Hydroxyethyl)-3-(3,4-dichlorophenyl)piperidine (−)

The (−) enantiomer is obtained by following the above procedure, starting from D(−)-tartaric acid.

M.p.=139° C.

$[\alpha]_D^{20}=-8.4°$ (c=1, $CH_3OH$).

II—PREPARATION OF COMPOUND 32

A) 3-(2-Hydroxyethyl)-3-(3,4-dichlorophenyl)-1-tert-butyl-carbamoylpiperidine 12.4 g of di-tert-butyl dicarbonate are added to solution of 13 g of 3-(2-hydroxyethyl)-3-(3,4-dichlorophenyl)piperidine (+) in 100 ml of dioxane. The mixture is then stirred for 1 hour at 40° C. It is evaporated to dryness and the residue is taken up in ether and washed with water, then a buffer solution of pH 2 and finally water. The ether phase is dried over $Na_2SO_4$, filtered and evaporated to dryness. The residue is purified by chromatography on silica gel using $CH_2Cl_2/CH_3OH$ 100/2 (v/v) as the eluent. 16.7 g of the expected product are thus obtained in the form of an oil after concentration of the pure fractions.

B) 3-Methanesulfonyloxyethyl-3-(3,4-dichlorophenyl)-1-tert-butylcarbamoylpiperidine 5.5 g of mesyl chloride are added dropwise to a solution of 16.5 g of the product prepared above in 100 ml of methylene chloride, in the presence of 4.9 g of triethylamine. The mixture is stirred for half an hour at room temperature and evaporated to dryness and the residue is taken up in ether, washed with water, dried over $Na_2SO_4$ and concentrated under vacuum to give 19 g of an oil.

C) 3-[2-(4-Benzylpiperidin-1-yl)ethyl]-3-(3,4-dichlorophenyl)-1-tert-butylcarbamoylpiperidine A solution of 18 g of the above product and 14 g of 4-benzylpiperidine in 40 ml of dimethylformamide is heated at 80° C. for 3 hours. The dimethylformamide is then evaporated off, the residue is taken up in water and extracted with ether and the extract is washed with water, dried over $Na_2SO_4$ and concentrated under vacuum. The residue is purified by chromatography on silica gel using $CH_2Cl_2/CH_3OH$ 100/3 (v/v) as the eluent. The pure fractions are concentrated under vacuum.

m=15 g.

D) 3-[2-(4-Benzylpiperidin-1-yl)ethyl]-3-(3,4-dichlorophenyl)piperidine (−) dihydrochloride 15 g of the above product dissolved in 75 ml of methanol, 60 ml of concentrated hydrochloric acid and 15 ml of water are stirred at room temperature for 1 hour. The mixture is evaporated to dryness, the residue is taken up in 100 ml of methylene chloride and the product is precipitated in ether. The precipitate is filtered off, washed with ether and dried under vacuum.

m=11.5 g.

M.p.=175° C.

$[\alpha]_D^{20}=-2.2°$ (c=1, $CH_3OH$)

E) Compound 32

10.6 g of BOP are added to a solution of 11 g of the above product, 6.09 g of triethylamine and 4.65 g of 3-isopropoxyphenylacetic acid in 100 ml of methylene chloride. The mixture is stirred at room temperature for 1 hour and evaporated to dryness and the residue is taken up in ethyl acetate, washed with water, dried over $Na_2SO_4$, filtered and concentrated under vacuum. The residue is purified by chromatography on silica gel using $CH_2Cl_2/CH_3OH$ 100/5 (v/v) as the eluent. The pure fractions are concentrated under vacuum, the hydrochloride is prepared in $CH_2Cl_2$ by the addition of ether saturated with hydrochloric acid, the mixture is evaporated to dryness, the residue is crystallized from isopropyl ether and the crystals are filtered off, washed with ether and dried under vacuum.

m=11.4 g.

M.p.=105° C.

$[\alpha]_D^{20}=-2.9°$ (c=1, $CH_3OH$).

EXAMPLE 33

3-[2-(4-Benzylpiperidin-1-yl)ethyl]-3-(3,4-dichlorophenyl)-1-(3-isopropoxyethyl)acetylpiperidine (+) hydrochloride

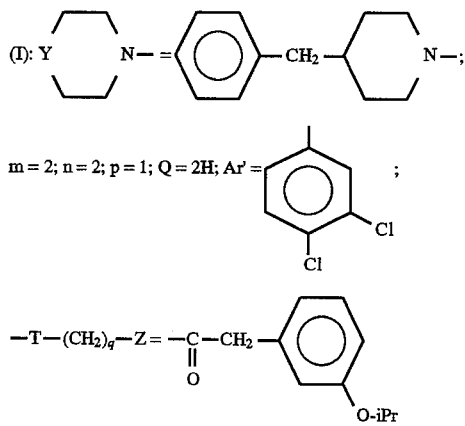

The above compound 33, (+) enantiomer, is obtained by following the procedure of Example 32, using the (−) enantiomer of 3-(2-hydroxyethyl)-3-(3,4-dichlorophenyl) piperidine as the starting material.

M.p.=105° C.

$[\alpha]_D^{20}=+3.0°$ (c=1, $CH_3OH$).

EXAMPLE 34

3-[2-(4-Hydroxy-4-phenylpiperidin-1-yl)ethyl]-3-(3,4-dichlorophenyl)-1-benzoylpiperidine (−) hydrochloride

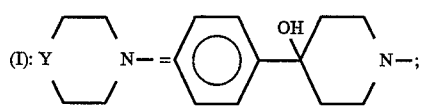

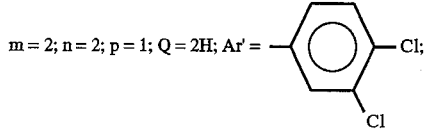

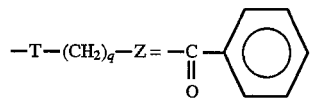

A) 3-[2-(4-Hydroxy-4-phenylpiperidin-1-yl)ethyl]-3-(3,4-dichlorphenyl)-1-tert-butylcarbamoylpiperidine A solution of 0.9 g of 3-methanesulfonyloxyethyl-3-(3,4-dichlorophenyl)-1-tert-butylcarbamoylpiperidine, prepared according to Example 32, step B), and 0.88 g of 4-hydroxy-4-phenylpiperidine in 3 ml of dimethylformamide is heated at 80° C. for 2 hours. It is evaporated to dryness, the residue is taken up in water and extracted with AcOEt and the extract is washed with a saturated aqueous solution of NaCl, dried over $MgSO_4$ and evaporated to dryness. The residue is purified by chromatography on silica gel using $CH_2Cl_2/CH_3OH$ 100/2 (v/v) as the eluent. The pure fractions are concentrated to give 0.8 g of an oil.

B) 3-[2-(4-Hydroxy-4-phenylpiperidin-1-yl)ethyl]-3-(3,4-dichlorophenyl)piperidine 0.8 g of the above product dissolved in 5 ml of methanol, 4 ml of concentrated hydrochloric acid and 1 ml of water is stirred for 1 hour at room temperature. The mixture is then evaporated to dryness and the residue is used as such for the next step.

m=0.77 g.

C) Compound 34

0.26 g of benzoyl chloride is added to a solution of 0.77 g of the above product and 0.3 g of triethylamine in 30 ml of methylene chloride. The reaction mixture is stirred for 1 hour at room temperature and evaporated to dryness and the residue is taken up in ethyl acetate, washed with water, dried over $Na_2SO_4$ and evaporated to dryness. The residue is purified by chromatography on silica gel using $CH_2Cl_2/CH_3OH$ 100/3 (v/v) as the eluent. The pure fractions are concentrated and taken up in $CH_2Cl_2$ and the hydrochloride is prepared by the addition of ether saturated with hydrochloric acid. The mixture is evaporated to dryness, the residue is crystallized from ether and the crystals are filtered off, washed with ether and dried under vacuum.

m=0.2 g.

M.p.=176° C.

$[\alpha]_D^{20}=-32.0°$ (c=1, $CH_3OH$).

EXAMPLE 35

3-[2-(4-Hydroxy-4-phenylpiperidin-1-yl)ethyl]-3-(3,4-dichlorophenyl)-1-benzoylpiperidine (+) hydrochloride

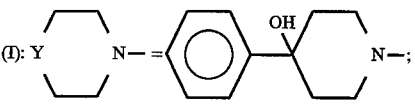

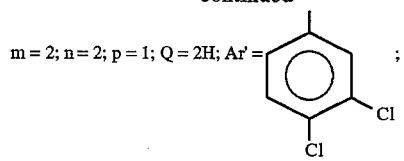

m = 2; n = 2; p = 1; Q = 2H; Ar' =

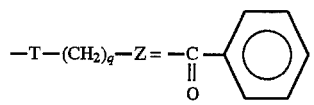

—T—(CH₂)$_q$—Z =

The above (+) enantiomer is obtained by following the procedure of Example 34, starting from 3-(2-hydroxyethyl)-3-(3,4-dichlorophenyl)piperidine (−).

M.p.=176° C.

[α]$_D^{20}$=+32.5° (c =1, CH₃OH).

EXAMPLE 36

N(a)-Methyl-3-[2-(4-benzyl-1-piperidinium)ethyl]-3-(3,4-dichlorophenyl)-1-(3-isopropoxyphenyl)acetylpiperidine iodide

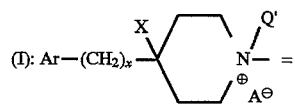

(I): Ar—(CH₂)$_x$—

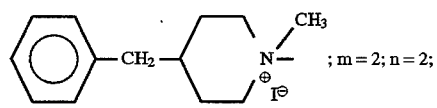

; m = 2; n = 2;

p = 1; Q = 2H; Ar' =

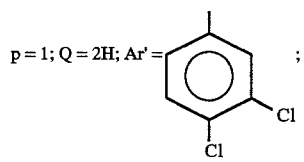

—T—(CH₂)$_q$—Z =

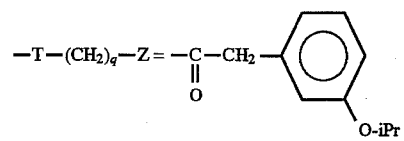

A solution of 1 g of the product described in Example 14 in 10 ml of methyl iodide is stirred at room temperature for 24 hours. It is then concentrated under vacuum. The residue is chromatographed on silica gel using CH₂Cl₂/CH₃OH 100/3 (v/v) as the eluent. The first product eluted corresponds to that in which the methyl located on nitrogen (b) of the 4-benzylpiperidine is in the axial position.

m=0.35 g.

¹³C NMR spectrum:

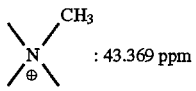

: 43.369 ppm

EXAMPLE 37

N(e)-Methyl-3-[2-(4-benzyl-1-piperidinium)ethyl]-3-(3,4-dichlorophenyl)-1-(3-isopropoxyphenyl)acetylpiperidine iodide

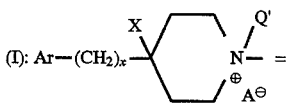

(I): Ar—(CH₂)$_x$—

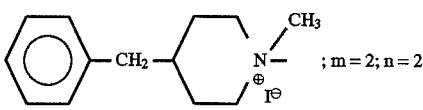

; m = 2; n = 2;

p = 1; Q = 2H; Ar' =

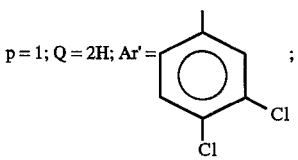

—T—(CH₂)$_q$—Z =

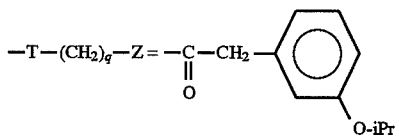

The product in which the methyl on nitrogen (b) of the 4-benzylpiperidine is in the equatorial position is obtained by following the procedure of Example 36 described above, collecting the second fraction eluted.

m=0.15 g.

¹³C NMR spectrum:

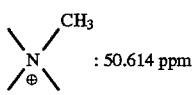

: 50.614 ppm

The quaternary ammonium salts described in Table V below are prepared by following the procedure of Examples 36 and 37 above.

TABLE V

[Structure shown at top of table: benzyl-CH₂-piperidine-N⁺(Q')(CH₂)₂-piperidine(3,4-dichlorophenyl)-N-C(=O)-CH₂-phenyl(Z)]

| Example n° | Q'(conformation) | A⁻ | z | M.p.; °C. |
|---|---|---|---|---|
| 38 | CH₂-phenyl (a) | Br⁻ | —O-iPr | 124 |
| 39 | CH₂-phenyl (e) | Br⁻ | —O-iPr | 144 |
| 40 | —C₂H₅ (a) | I⁻ | —O-iPr | 116 |
| 41 | —C₂H₅ (e) | I⁻ | —O-iPr | 122 |
| 42 | —CH₃ (a) | I⁻ | —OC₂H₅ | 120 |
| 43 | —CH₃ (e) | I⁻ | —OC₂H₅ | 126 |

EXAMPLE 44

N(a)-Methyl-3-[2-(4-benzyl-1-piperidinium)ethyl]-3-(3,4-dichlorophenyl)-1-(3-isopropoxyphenyl)acetylpiperidine (−) chloride

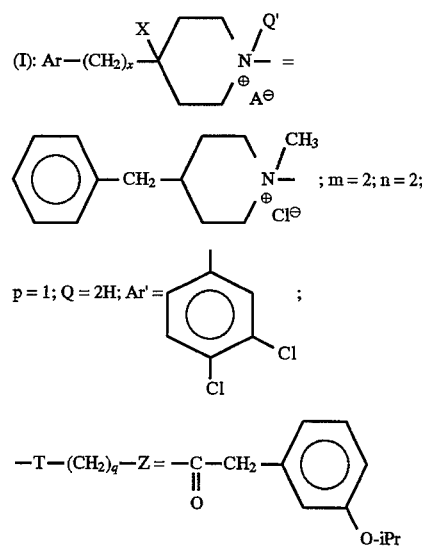

A) Preparation of the iodide derivative

A solution of 10 g of the product described in Example 32 in 50 ml of methyl iodide is stirred at room temperature for 2 hours. It is evaporated to dryness and the residue is chromatographed on silica gel using CH₂Cl₂/CH₃OH 100/3 (v/v) as the eluent. The conformational isomer which is eluted first corresponds to that in which the methyl is in the axial position on nitrogen (b) of the 4-benzylpiperidine.

B) Preparation of the chloride derivative

The iodide ion is then exchanged with the chloride ion by eluting the product on an Amberlite IRA68 ion exchange resin.

This gives 5.6 g of the quaternary ammonia chloride.

M.p.=103° C.
$[\alpha]_D^{20}=-12.8°$ (c=1, CH₃OH).

EXAMPLE 45

N(a)-Methyl-3-[2-(4-benzyl-1-piperidinium)ethyl]-3-(3,4-dichlorophenyl)-1-(3-isopropoxyphenyl)acetylpiperidine (+) chloride

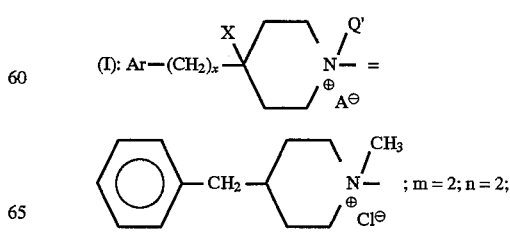

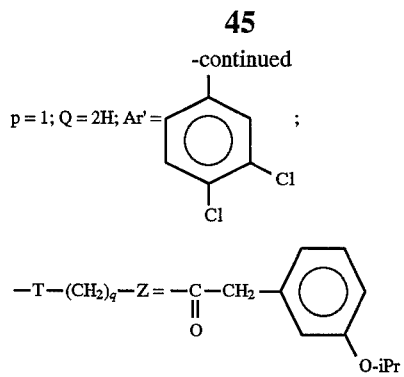

8.9 g of the expected quaternary ammonium salt are obtained by following an identical procedure to Example 44, starting from the product described in Example 33.

M.p.=104° C.

$[\alpha]_D^{20}$=+13.0° (c=1, CH$_3$OH).

EXAMPLE 46

N(e)-Methyl-3-[2-(4-benzyl-1-piperidinium)-ethyl]-3-(3, 4-dichlorophenyl)-1-(3-isopropoxyphenyl)acetylpiperidine (−) iodide

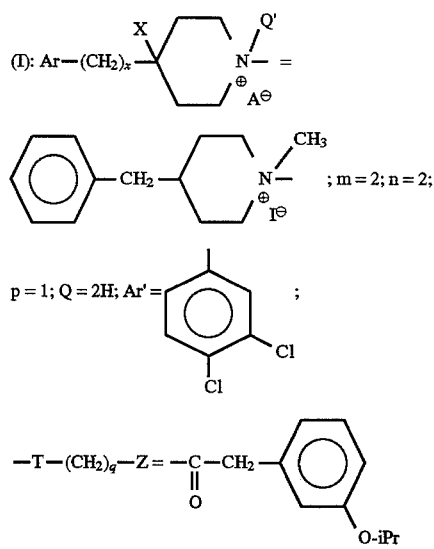

The enantiomer in which the methyl on nitrogen (b) of the 4-benzylpiperidine is in the equatorial position is obtained by following the procedure of Example 44 A), collecting the second fraction eluted. This gives 2.6 g of the quaternary ammonium salt.

M.p.=110° C.

$[\alpha]_D^{20}$=−0.1° (c=1, CH$_3$OH)

EXAMPLE 47

N(e)-Methyl-3-[2-(4-benzyl-1-piperidinium)ethyl]-3-(3, 4-dichlorophenyl)-1-(3-isopropoxyphenyl)acetylpiperidine (+) iodide

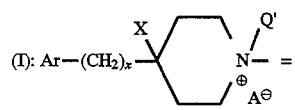

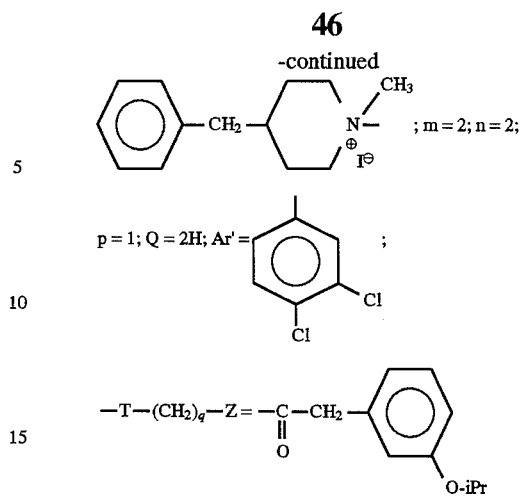

The expected product is obtained by following the procedure of Example 46, starting from the product described in Example 33.

M.p.=110° C.

$[\alpha]_D^{20}$=+0.1° (c=1, CH$_3$OH)

EXAMPLE 48

3-[2-(4-Benzyl-1-piperidinium)ethyl]-3-(3,4-dichlorophenyl)-1-(3-isopropoxyphenyl)acetylpiperidine N-oxide

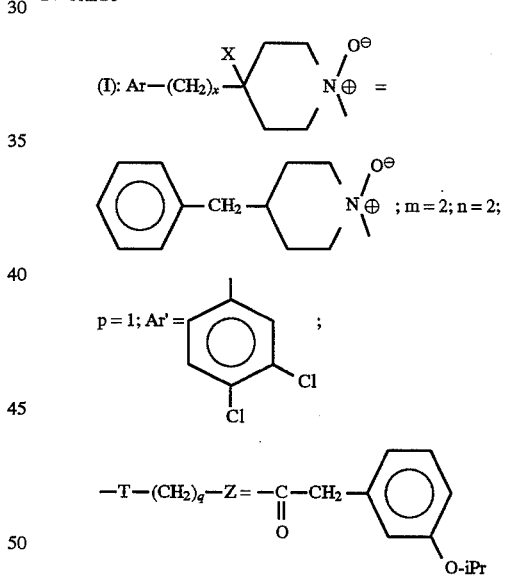

2 g of the free base of the compound of Example 14 are dissolved in 20 ml of tetrahydrofuran. 1.1 g of metachloroperbenzoic acid are added and the reaction mixture is stirred for 2 hours at room temperature. It is concentrated under vacuum to a volume of 5 ml and the residue is diluted in 10 ml of methylene chloride. The solution is washed twice with a saturated solution of NaHCO$_3$, decanted, dried over MgSO$_4$ and concentrated under vacuum. The residue is chromatographed on silica gel using CH$_2$Cl$_2$/CH$_3$OH 100/5 (v/v) as the eluent. The pure product fractions are concentrated under vacuum and the residue is crystallized from isopropyl ether.

m=1.47 g.

M.p.=135° C.

EXAMPLE 49

3-[2-(4-Benzylpiperidin-1-yl)ethyl]-3-(3,4-dichlorophenyl)piperidine dihydrochloride Synthesis intermediate of formula (II).

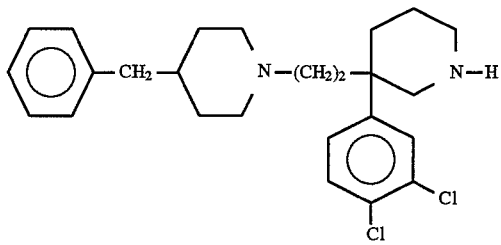

A) 4-(4-Benzylpiperidin-1-yl)-2-(3,4-dichlorophenyl)butyronitrile 23.5 g of sodium amide are added in small portions to a solution of 94 g of 3,4-dichlorophenylacetonitrile in 500 ml of anhydrous ether. The mixture is subsequently stirred for 1 hour at room temperature and then for 3 hours under reflux. It is cooled to 0° C. and a solution of 129 g of 2-(4-benzylpiperidin-1-yl)-1-chloroethane in 300 ml of ether is added dropwise. The reaction mixture is allowed to return to room temperature and then refluxed for 3 hours. It is cooled and poured into 600 ml of water and the organic phase is decanted, washed with water and extracted twice with 500 ml of a 15% solution of HCl. The aqueous phase is stirred and the product precipitates in the form of the hydrochloride. This is filtered off, washed with water and dried under vacuum. The residue is recrystallized from 600 ml of isopropanol to give 95 g of crystals.

The product is taken up in water and the solution is neutralized with a solution of NaOH. The mixture is extracted with ether and the extract is washed with water, dried over $Na_2SO_4$ and evaporated to dryness to give 87 g of an oil.

B) Ethyl γ-[2-(4-benzylpiperidin-1-yl)ethyl]-γ-cyano-3,4-dichloroenzylbutanoate

A solution of 87 g of the product described above, 28 g of ethyl acrylate and 2.5 ml of triton B in 45 ml of dioxane is heated for 24 hours at 80° C. It is cooled, taken up in ether, washed with water, dried over $Na_2SO_4$ and evaporated to dryness to give 109.5 g of an oil.

C) 5-[2-(4-Benzylpiperidin-1-yl)ethyl]-5-(3,4-dichlorophenyl)piperidone

A solution of 100 g of the product prepared above in 1.5 liters of ethanol is hydrogenated at 60° C. and at atmospheric pressure in the presence of Raney Ni. When the volume of hydrogen has been consumed, the catalyst is filtered off, the filtrate is evaporated to dryness and the residue is taken up in methylene chloride, washed with water and dried over $Na_2SO_4$. The hydrochloride is then formed and recrystallized from 220 ml of isopropanol. The crystals are filtered off and dried under vacuum. The product is taken up in water, neutralized with a solution of NaOH and extracted with ether and the extract is dried over $Na_2SO_4$ to give 44 g of an oil.

D) Compound 49

A solution of 44 g of the above product in 200 ml of tetrahydrofuran is added dropwise to a suspension of 9.4 g of lithium aluminum hydride in 250 ml of tetrahydrofuran, heated to 60° C. Refluxing is continued for 3 hours. The mixture is cooled in ice, and 10 ml of water, 10 ml of 4 N NaOH and 30 ml of water are added in succession. The inorganic material is filtered off, the filtrate is evaporated to dryness, the residue is taken up in methylene chloride and the hydrochloride is prepared. The mixture is evaporated to dryness, the residue is triturated in pentane and the product is filtered off and dried under vacuum.

m=35 g.

M.p.=170° C.

EXAMPLE 50

3-[2-(4-Benzylpiperidin-1-yl)ethyl]-3-(3,4-dichlorophenyl)-1-(2-phenyl-2-methoxy)acetylpiperidine hydrochloride Diastereoisomer of lower polarity.

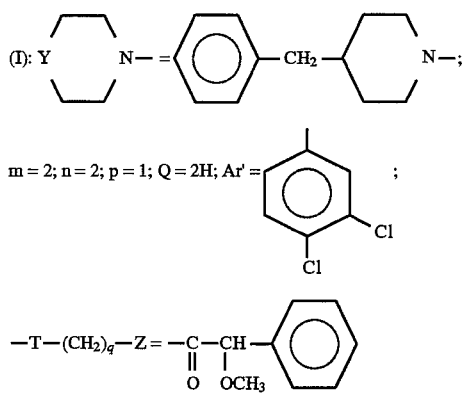

1.5 g of the diamine prepared in Example 49, 1.06 g of triethylamine, 0.55 g of (±)-α-methoxyphenylacetic acid and 1.6 g of BOP in 25 ml of methylene chloride are stirred for 2 hours. The mixture is evaporated to dryness and the residue is taken up in ethyl acetate, washed with water, dried over $Na_2SO_4$ and evaporated to dryness. The residue is purified by chromatography on silica gel using $CH_2Cl_2/CH_3OH$ 100/0.5 (v/v) as the eluent. The product which is eluted first is the expected product. The fractions are concentrated under vacuum and taken up in $CH_2Cl_2$, the hydrochloride is prepared, the mixture is evaporated to dryness, the residue is triturated in pentane and the product is filtered off and dried under vacuum.

m=0.50 g.

M.p.=134° C.

EXAMPLE 51

3-[2-(4-Benzylpiperidin-1-yl)ethyl]-3-(3,4-dichlorophenyl)-1-(2-phenyl-2-methoxy)acetylpiperidine hydrochloride Diastereoisomer of higher polarity.

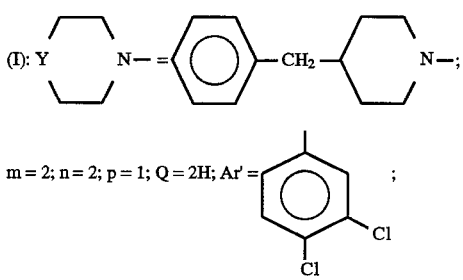

-continued

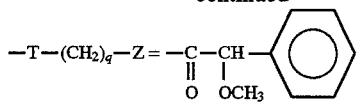

The diastereoisomer of higher polarity is obtained by following the procedure of Example 50, using a 100/2 (v/v) $CH_2Cl_2/CH_3OH$ mixture as the eluent. The hydrochloride is prepared in methylene chloride, the mixture is evaporated to dryness and the residue is taken up in pentane.

m=0.50 g.

M.p.=118° C.

The pairs of diastereoisomers 52/53, 54/55 and 56,57 described in Table VI below are prepared by following the procedure of Examples 50 and 51.

The reactant α-hydroxy-3-isopropoxyphenylacetic acid used to prepare the compounds of Examples 56 and 57 iS a novel product and can be prepared as indicated below.

α-Hydroxy-3-isopropoxyphenylacetic acid

Step 1

60 g of $K_2CO_3$ and then 60 ml of 2-iodopropane are added to a solution of 50 g of 3-hydroxybenzaldehyde in 250 ml of DMF.

The reaction mixture is heated at 50° C. for 18 hours. The mixture obtained is poured into 2.5 l of water and extracted with ether, the extract is washed with a dilute solution of NaOH and then water and dried over $MgSO_4$ and the solvent is evaporated off to give 53.5 g of a liquid residue.

Step 2

53 g Of the product obtained according to step 1 above are added to a solution of 38 g of sodium bisulfite in 120 ml of water. The mixture is stirred for 20 hours and a solution of 44.2 g of potassium cyanide in 90 ml of water is then added at 20° C.

After 2 hours the mixture is extracted with ether, the extract is washed with water and dried over $MgSO_4$ and the solvent is evaporated off under vacuum. The residue is chromatographed on silica gel using heptane/ethyl acetate 100/30 (v/v) as the eluent. 57 g of product are recovered in the form of an oil.

Step 3

46 g of the product obtained according to step 2 above are added to 50 ml of water and 50 ml of concentrated HCl. The mixture is heated at 110° C. for 1 hour. After cooling, it is extracted with ether and the extract is washed with water. The acid is extracted with a dilute solution of NaOH. The aqueous phase is acidified and extracted with ether, the extract is dried over $MgSO_4$ and the solvents are evaporated off. The acid is crystallized from a 1/2 (v/v) toluene/pentane mixture.

m=27.5 g.

EXAMPLE 58

3-[2-(4-Benzylpiperidin-1-yl)ethyl]-3-(3,4-dichlorophenyl)-1-[2-(3-chlorophenyl)-2-hydroxy]acetylpiperidine (+) hydrochloride

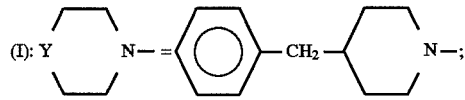

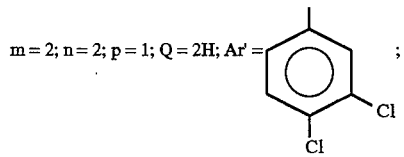

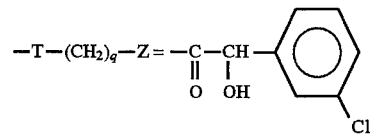

A solution of 0.67 g of 3-[2-(4-benzylpiperidin-1-yl) ethyl]-3-(3,4-dichlorophenyl)piperidine (−) dihydrochloride described in Example 32, step D, 0.17 g of triethylamine, 0.32 g of S(+)-α-hydroxy-3-chlorophenylacetic acid and 0.82 g of BOP in 10 ml of methylene chloride is stirred for 2 hours. It is evaporated to dryness and the residue is taken up in ethyl acetate, washed with water, dried over $Na_2SO_4$ and concentrated under vacuum. The residue is purified by chromatography on silica gel using $CH_2Cl_2/CH_3OH$ 100/1.5 (v/v) as the eluent. The pure fractions are concentrated under vacuum and taken up in methylene chloride, the hydrochloride is prepared, the mixture is evaporated to dryness and the residue is taken up in pentane. The product is filtered off, washed with ether and dried under vacuum.

m=0.40 g.

M.p.=122° C.

$[\alpha]_D^{20}$=+68.4° (c=1, $CH_3OH$).

EXAMPLE 59

3-[2-(4-Benzylpiperidin-1-yl)ethyl]-3-(3,4-dichlorophenyl)-1-[2-(3-chlorophenyl)-2-hydroxy]acetylpiperidine (−) hydrochloride

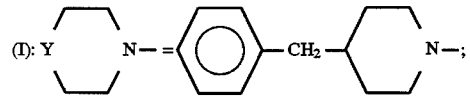

TABLE VI

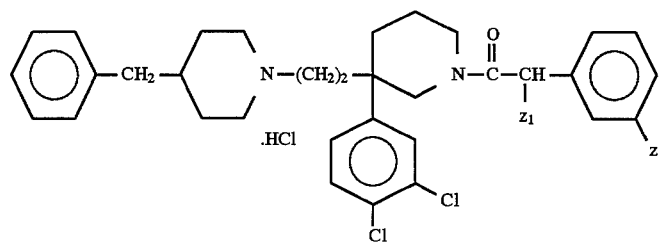

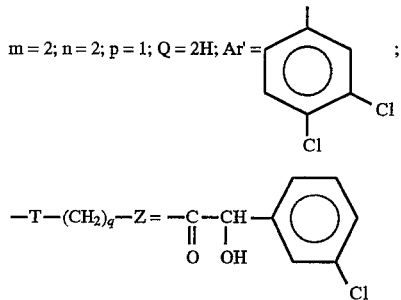

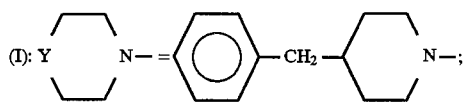

The expected product is obtained by following the procedure of Example 58, starting from 3-[2-(4-benzylpiperidin-1-yl)ethyl]-3-(3,4-dichlorophenyl)piperidine (+) prepared according to Example 32, step D, from 3-(2-hydroxyethyl)-3-(3,4-dichlorophenyl)piperidine (−) described in step C of the preparation of the optically pure amino alcohol, and with R(−)-α-hydroxy-3-chlorophenylacetic acid.

m=0.50 g.
M.p.=122° C.
$[\alpha]_D^{20}=-74°$ (c=1, CH$_3$OH).

EXAMPLE 60

3-[2-(4-Benzylpiperidin-1-yl)ethyl]-3-(3,4-dichlorophenyl)-1-[2-(3-chlorophenyl)-2-hydroxy]acetylpiperidine (−) hydrochloride

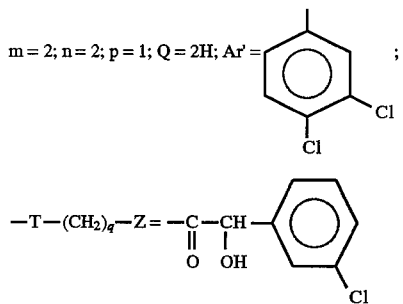

A solution of 0.67 g of 3-[2-(4-benzylpiperidin-1-yl)ethyl]-3-(3,4-dichlorophenyl)piperidine (−), 0.32 g of R(−)-α-hydroxy-3-chlorophenylacetic acid, 0.17 g of triethylamine and 0.82 g of BOP in 50 ml of methylene chloride is stirred at room temperature for 2 hours. The expected product is obtained by subsequently following the procedure of Example 58.

m=0.40 g.
M.p.=128° C.
$[\alpha]_D^{20}=-34°$ (c=1, CH$_3$OH).

EXAMPLE 61

3-[2-(4-Benzylpiperidin-1-yl)ethyl]-3-(3,4-dichlorophenyl)-1-[2-(3-chlorophenyl)-2-hydroxy]acetylpiperidine (+) hydrochloride

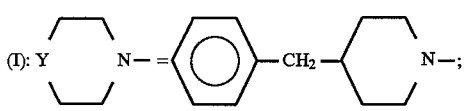

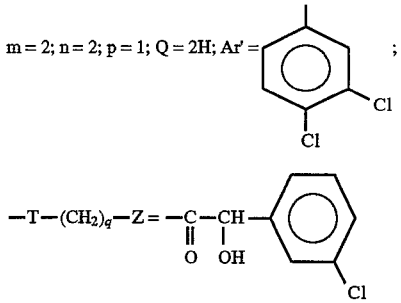

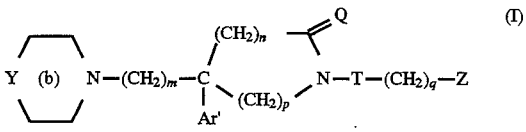

The expected product is obtained by following the procedure of Example 58, starting from S(+)-α-hydroxy-3-chlorophenylacetic acid and 3-[2-(4-benzyl-piperidin-1-yl)ethyl]-3-(3,4-dichlorophenyl)piperidine (+) prepared according to Example 32, step D, from 3-(2-hydroxyethyl)-3-(3,4-dichlorophenyl)piperidine (−) described in step C of the preparation of the optically pure amino alcohol.

m=0.4 g.
M.p.=127° C.
$[\alpha]_D^{20}=+35°$ (c=1, CH$_3$OH).

What is claimed is:

1. A method of preparing a compound of formula (I),

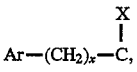

in which:

Y is either a group Cy-N or Cy-CH$_2$-N, in which:

Cy is a phenyl which is unsubstituted or monosubstituted or polysubstituted by a substituent selected from the group consisting of hydrogen, a halogen atom, a hydroxyl, a C$_1$-C$_4$ alkoxy, a C$_1$-C$_4$ alkyl and a trifluoromethyl, said substituents being identical or different; a C$_3$-C$_7$ cycloalkyl group; a pyrimidyl group or a pyridyl group;

or a group $$Ar-(CH_2)_x-\overset{\overset{\displaystyle X}{|}}{C},$$

in which:

Ar is a phenyl which is unsubstituted or monosubstituted or polysubstituted by a substituent selected from the group consisting of hydrogen, a halogen atom, a hydroxyl, a C$_1$-C$_4$ alkoxy, a trifluoromethyl and a C$_1$-C$_4$ alkyl, said substituents being identical or different; a pyridyl group or a thienyl group;

x is zero or one; and

X is a hydrogen: a hydroxyl; a C$_1$-C$_4$ alkoxy; a C$_1$-C$_4$ acyloxy; a carboxyl;

a C$_1$-C$_4$ carbalkolxy; a cyano; a group —N(X$_1$)$_2$, in which the groups X$_1$ independently are hydrogen, a C$_1$-C$_4$ alkyl, a C$_1$-C$_4$ hydroxyalkyl or a C$_1$-C$_4$ acyl, or else —(X$_1$)$_2$, forms, with the nitrogen atom to which it is bonded, a heterocycle selected from the group consisting of pyrrolidine, piperidine and morpholine; or a group -S-$X_2$, in which $X_2$ is hydrogen or a $C_1$-$C_4$ alkyl group; or else X is a double bond between the carbon atom to which it is bonded and the adjacent carbon atom in the heterocycle;

m is 2 or 3;

Ar' is a phenyl which is unsubstituted or monosubstituted or polysubstituted by a substituent selected from the group consisting of hydrogen, a halogen atom, a trifluoromethyl, a $C_1$-$C_4$ alkoxy and a $C_1$-$C_4$ alkyl, said substituents being identical or different; a thienyl; a benzothienyl; a naphthyl or an indolyl;

n is 0, 1, 2 or 3;

p is 1 or 2, and when p is equal to 2, n is then equal to 1 and Q is two hydrogen atoms;

Q is oxygen or two hydrogen atoms;

T is a group selected from $$-\underset{\underset{O}{\|}}{C}- \quad \text{and} \quad -CH_2-$$

q is 0, 1, 2 or 3; and

Z is phenyl which is unsubstituted or monosubstituted or polysubstituted by a substituent selected from the group consisting of a halogen atom, a trifluoromethyl, a $C_1$-$C_4$ alkyl, a hydroxyl and a $C_1$-$C_4$ alkoxy; a naphthyl which is unsubstituted or monosubstituted or polysubstituted by a substituent selected from the group consisting of a halogen, a trifluoromethyl, a $C_1$-$C_4$ alkyl and a hydroxyl; a pyridyl; a thienyl; an indolyl; a quinolyl; a benzothienyl; an imidazolyl; said pyridyl, thienyl, indolyl, quinolyl, benzothienyl or imidazolyl groups being unsubstituted or monosubstituted or polysubstituted by a $C_1$-$C_4$ alkyl or hydroxyl; or else when T is —C=O, —(CH$_2$)$_q$—Z represents a group where q=0, and Z is a benzyl group substituted on the $$-\underset{|}{CH}-$$

of the benzyl group by a substituent selected from the group consisting of a hydroxyl, a $C_1$-$C_4$ alkoxy and a $C_1$-$C_4$ alkyl, and the benzyl group is unsubstituted or substituted on the aromatic ring by a substituent selected from the group consisting of a halogen, a trifluoromethyl, a $C_1$-$C_4$ alkyl, a hydroxyl and a $C_1$-$C_4$ alkoxy;

or a salt thereof with a mineral or organic acid, or, when $$Y = Ar-(CH_2)_x-\underset{\underset{|}{|}}{\overset{X}{C}}$$

a quaternary ammonium salt thereof, formed with nitrogen (b) of the piperdine, or an N-oxide derivative formed with this same nitrogen atom. said method comprising:

a) treating a compound of the formula $$E-(CH_2)_m-\underset{\underset{Ar'}{|}}{\overset{(CH_2)_n}{\underset{(CH_2)_p}{C}}}\overset{Q}{\underset{}{\diagdown}}N\diagdown H \qquad (II)$$

in which m, Ar', n, p and Q are as defined above and E is a hydroxyl, an O-protected group or a group $$Y\diagup\overline{\phantom{xx}}\diagdown N-$$

in which Y is as defined above, it being understood that: when Y is the group $$Ar-(CH_2)_x-\underset{\underset{|}{|}}{\overset{X}{C}}$$

in which X is a hydroxyl, this hydroxyl can be protected, either with a functional derivative of an acid of the formula $$HO-\underset{\underset{O}{\|}}{C}-(CH_2)_q-Z \qquad (III)$$

in which q and Z are as defined above, when a compound of formula (I) in which T is —CO— is to be prepared, or with a halogenated derivative of the formula $$Hal-(CH_2)_{q+1}-Z \qquad (IV)$$

in which q and Z are as defined above and Hal is a halogen when a compound of formula (I) in which T is —CH$_2$— is to be prepared, to give the compound of the formula $$E-(CH_2)_m-\underset{\underset{Ar'}{|}}{\overset{(CH_2)_n}{\underset{(CH_2)_p}{C}}}\overset{Q}{\underset{}{\diagdown}}N-T-(CH_2)_q-Z \qquad (V)$$

b) then, when E is a tetrahydropyranyloxy group, remaining the tetrahydropyranyloxy group by reaction with an acid, c) treating the resulting alcohol of the formula $$HO-(CH_2)_m-\underset{\underset{Ar'}{|}}{\overset{(CH_2)_n}{\underset{(CH_2)_p}{C}}}\overset{Q}{\underset{}{\diagdown}}N-T-(CH_2)_q-Z \qquad (VI)$$

with methanesulfonyl chloride, d) reacting the resulting mesylate of the formula $$CH_3SO_2-O-(CH_2)_m-\underset{\underset{Ar'}{|}}{\overset{(CH_2)_n}{\underset{(CH_2)_p}{C}}}\overset{Q}{\underset{}{\diagdown}}N-T-(CH_2)_q-Z \qquad (VII)$$

with a secondary amine of the formula $$Y\diagup\overline{\phantom{xx}}\diagdown NH$$

in which Y is as defined above, and e) when X is a protected hydroxyl, deprotecting the hydroxyl group, and optionally converting the resulting product to one of its salts with mineral or organic acids, or f) when Y is the group

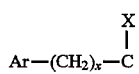

optionally converting the resulting product to one of its quaternary ammonium salts formed with nitrogen (b) of the piperidine, or to an N-oxide derivative formed with this same nitrogen atom.

2. The method according to claim 1, wherein the halogen in the definition of Ar', and the halogen in the definition of Z referring to substitution of the phenyl and the benzyl groups, is chlorine or fluorine.

3. The method according to claim 1, wherein Hal in formula (IV) is chlorine or bromine.

4. The method according to claim 1, wherein E is an O-protected group.

5. The method according to claim 4, wherein said O-protected group is tetrahydropyran-2-yloxy.

* * * * *